(12) United States Patent
Dar et al.

(10) Patent No.: US 8,209,022 B2
(45) Date of Patent: *Jun. 26, 2012

(54) GAIT MODULATION SYSTEM AND METHOD

(75) Inventors: Amit Dar, Kfar Hess (IL); Yossef Shalev, Raanana (IL); Jonathan Bar-Or, Pardes Hanna (IL); Roger Nathan, Herzlia (IL)

(73) Assignee: Bioness Neuromodulation Ltd., Raanana (IL)

( * ) Notice: Subject to any disclaimer, the term of this patent is extended or adjusted under 35 U.S.C. 154(b) by 946 days.

This patent is subject to a terminal disclaimer.

(21) Appl. No.: 12/096,077

(22) PCT Filed: Nov. 16, 2006

(86) PCT No.: PCT/IL2006/001326
§ 371 (c)(1),
(2), (4) Date: Jun. 25, 2008

(87) PCT Pub. No.: WO2007/057899
PCT Pub. Date: May 24, 2007

(65) Prior Publication Data
US 2009/0177131 A1    Jul. 9, 2009

Related U.S. Application Data

(60) Provisional application No. 60/736,858, filed on Nov. 16, 2005, provisional application No. 60/746,060, filed on May 1, 2006, provisional application No. 60/805,359, filed on Jun. 21, 2006.

(51) Int. Cl.
*A61N 1/00*    (2006.01)
(52) U.S. Cl. .............................. 607/48; 607/49; 607/144
(58) Field of Classification Search .................. 607/144
See application file for complete search history.

(56) References Cited

U.S. PATENT DOCUMENTS

| 1,422,396 | A | 7/1922 | Wappler |
| 1,644,803 | A | 10/1927 | Wappler |

(Continued)

FOREIGN PATENT DOCUMENTS

DE      19830359 A1      1/2000

(Continued)

OTHER PUBLICATIONS

International Preliminary Report on Patentability for PCT/IL07/00531, mailed Mar. 10, 2009, 4 pages.

(Continued)

*Primary Examiner* — Eric D. Bertram
(74) *Attorney, Agent, or Firm* — Cooley LLP

(57) ABSTRACT

An electrical stimulation orthosis and method therefor, the orthosis including: (a) an at least semi-rigid frame configured to substantially envelop a limb segment, the frame having at least one first complementary mechanical fastener associated therewith; (b) a surface electrical stimulation electrode assembly associated with, and supported by, the frame, the assembly having a surface stimulation electrode for contacting at least one stimulation point on the limb segment, the surface electrode assembly having an electrode base for electrically associating, via the frame, with a stimulator unit for providing a stimulation signal to the surface electrode, the electrode base having a top face for receiving the stimulation electrode, and a bottom face having at least one second complementary mechanical fastener, the first and second fasteners adapted for reversible attachment and detachment, at a plurality of locations on the frame, thereby enabling the electrical stimulation electrode assembly to be adjustably and reversibly positioned on the frame.

17 Claims, 31 Drawing Sheets

U.S. PATENT DOCUMENTS

| | | | |
|---|---|---|---|
| 3,204,637 | A | 9/1965 | Frank et al. |
| 3,426,748 | A | 2/1969 | Bowers |
| 3,881,496 | A | 5/1975 | Vredenbregt et al. |
| 3,941,137 | A | 3/1976 | Vredenbregt et al. |
| 4,558,704 | A | 12/1985 | Petrofsky |
| 4,580,569 | A | 4/1986 | Petrofsky |
| 4,647,918 | A | 3/1987 | Goforth |
| 4,697,808 | A | 10/1987 | Larson et al. |
| 4,745,930 | A | 5/1988 | Confer |
| 4,832,033 | A | 5/1989 | Maher et al. |
| 5,112,296 | A | 5/1992 | Beard et al. |
| 5,121,747 | A | 6/1992 | Andrews |
| 5,253,654 | A | 10/1993 | Thomas et al. |
| 5,277,697 | A | 1/1994 | France et al. |
| 5,285,781 | A | 2/1994 | Brodard |
| 5,323,650 | A | 6/1994 | Fullen et al. |
| 5,330,516 | A | 7/1994 | Nathan |
| 5,350,414 | A | 9/1994 | Kolen |
| 5,357,696 | A | 10/1994 | Gray et al. |
| 5,408,873 | A | 4/1995 | Schmidt et al. |
| 5,437,619 | A | 8/1995 | Malewicz et al. |
| 5,487,759 | A | 1/1996 | Bastyr et al. |
| 5,540,735 | A * | 7/1996 | Wingrove ............ 607/46 |
| 5,562,707 | A | 10/1996 | Prochazka et al. |
| 5,613,943 | A | 3/1997 | Palumbo |
| 5,643,332 | A | 7/1997 | Stein |
| 5,664,346 | A | 9/1997 | Barker |
| 5,748,845 | A | 5/1998 | Labun et al. |
| 5,775,332 | A | 7/1998 | Goldman |
| 5,814,093 | A | 9/1998 | Stein |
| 5,861,017 | A | 1/1999 | Smith et al. |
| 5,916,159 | A | 6/1999 | Kelly et al. |
| 5,951,598 | A | 9/1999 | Bishay et al. |
| 5,980,472 | A | 11/1999 | Seyl |
| 5,983,140 | A | 11/1999 | Smith et al. |
| 6,002,965 | A | 12/1999 | Katz et al. |
| 6,019,877 | A | 2/2000 | Dupelle et al. |
| 6,064,912 | A | 5/2000 | Kenney |
| 6,126,355 | A | 10/2000 | Clover, Jr. |
| 6,129,695 | A | 10/2000 | Peters et al. |
| 6,174,294 | B1 | 1/2001 | Crabb et al. |
| 6,179,799 | B1 | 1/2001 | Doran |
| 6,195,921 | B1 | 3/2001 | Truong |
| 6,246,863 | B1 | 6/2001 | Kampel |
| 6,282,448 | B1 | 8/2001 | Katz et al. |
| 6,308,102 | B1 | 10/2001 | Sieracki et al. |
| 6,349,126 | B2 | 2/2002 | Ogawa et al. |
| 6,438,428 | B1 | 8/2002 | Axelgaard et al. |
| 6,445,955 | B1 | 9/2002 | Michelson et al. |
| 6,456,884 | B1 | 9/2002 | Kenney |
| 6,456,885 | B1 | 9/2002 | Shiba et al. |
| 6,496,739 | B2 | 12/2002 | Arbel |
| 6,507,757 | B1 | 1/2003 | Swain et al. |
| 6,516,500 | B2 | 2/2003 | Ogino et al. |
| 6,564,103 | B2 | 5/2003 | Fischer et al. |
| 6,567,706 | B2 | 5/2003 | Bar-Or et al. |
| 6,571,115 | B2 | 5/2003 | Axelgaard et al. |
| 6,578,745 | B1 | 6/2003 | Taylor et al. |
| 6,607,500 | B2 | 8/2003 | Da Silva et al. |
| 6,618,624 | B2 | 9/2003 | Elias |
| 6,651,352 | B2 | 11/2003 | McGorry et al. |
| 6,692,453 | B2 | 2/2004 | Wolfe |
| D494,273 | S | 8/2004 | Haugland et al. |
| 6,829,510 | B2 | 12/2004 | Nathan et al. |
| 6,988,005 | B2 | 1/2006 | McGraw et al. |
| 7,011,637 | B2 | 3/2006 | Sherman et al. |
| 7,146,220 | B2 | 12/2006 | Dar et al. |
| 7,158,822 | B2 | 1/2007 | Payne, Jr. |
| 7,162,305 | B2 | 1/2007 | Tong et al. |
| 7,174,607 | B1 | 2/2007 | Buettell |
| 7,200,517 | B2 | 4/2007 | Darley et al. |
| 7,257,448 | B2 | 8/2007 | Crowe et al. |
| 7,337,007 | B2 | 2/2008 | Nathan et al. |
| 7,359,751 | B1 | 4/2008 | Erickson et al. |
| 7,403,821 | B2 | 7/2008 | Haugland et al. |
| 7,410,471 | B1 | 8/2008 | Campbell et al. |
| 7,416,537 | B1 | 8/2008 | Stark et al. |
| 7,899,556 | B2 | 3/2011 | Nathan et al. |
| 2003/0040788 | A1 | 2/2003 | Dupelle et al. |
| 2003/0050673 | A1 | 3/2003 | Yamazaki et al. |
| 2003/0065368 | A1 | 4/2003 | Van Der Hoeven |
| 2003/0083596 | A1 | 5/2003 | Kramer et al. |
| 2003/0114892 | A1 | 6/2003 | Nathan et al. |
| 2003/0144710 | A1 | 7/2003 | Haugland et al. |
| 2004/0011366 | A1 | 1/2004 | Schulman et al. |
| 2004/0122483 | A1 | 6/2004 | Nathan et al. |
| 2004/0147975 | A1 | 7/2004 | Popovic et al. |
| 2004/0173220 | A1 | 9/2004 | Harry et al. |
| 2004/0243197 | A1 | 12/2004 | Demian |
| 2004/0254624 | A1 | 12/2004 | Johnson |
| 2005/0049652 | A1 | 3/2005 | Tong |
| 2005/0085706 | A1 | 4/2005 | Perrault et al. |
| 2005/0131317 | A1 | 6/2005 | Oddsson et al. |
| 2005/0192645 | A1 | 9/2005 | Stein et al. |
| 2005/0261609 | A1 | 11/2005 | Collings et al. |
| 2006/0015470 | A1 | 1/2006 | Lauer et al. |
| 2006/0276704 | A1 | 12/2006 | McGinnis et al. |
| 2006/0282017 | A1 | 12/2006 | Avni et al. |
| 2006/0282018 | A1 | 12/2006 | Balzano |
| 2007/0021689 | A1 | 1/2007 | Stergiou et al. |
| 2007/0106343 | A1 | 5/2007 | Monogue et al. |
| 2007/0112285 | A1 | 5/2007 | Dar et al. |
| 2007/0112394 | A1 | 5/2007 | Nathan et al. |
| 2007/0179560 | A1 | 8/2007 | Tong et al. |
| 2007/0203533 | A1 | 8/2007 | Goren et al. |
| 2008/0033505 | A1 | 2/2008 | Davis et al. |
| 2008/0045872 | A1 | 2/2008 | Bauerfeind et al. |
| 2008/0046036 | A1 | 2/2008 | King et al. |
| 2008/0140154 | A1 | 6/2008 | Loeb et al. |
| 2008/0154113 | A1 | 6/2008 | Zilberman |
| 2008/0154335 | A1 | 6/2008 | Thrope et al. |
| 2008/0319349 | A1 | 12/2008 | Zilberman |
| 2009/0069865 | A1 | 3/2009 | Lasko et al. |
| 2011/0137375 | A1 | 6/2011 | McBride |
| 2011/0152968 | A1 | 6/2011 | Nathan et al. |

FOREIGN PATENT DOCUMENTS

| | | |
|---|---|---|
| EP | 1508302 | 2/2005 |
| JP | 1985-119949 A | 6/1985 |
| JP | 1994-501854 T | 3/1994 |
| JP | 2002-191580 A | 7/2002 |
| JP | 2004-503266 T | 2/2004 |
| JP | 2004-215735 A | 8/2004 |
| JP | 2004-313555 A | 11/2004 |
| JP | 2005-514143 T | 5/2005 |
| JP | 2006-166244 A | 6/2006 |
| WO | WO 2004/098703 | 11/2004 |
| WO | WO 2006/113801 | 10/2006 |

OTHER PUBLICATIONS

International Search Report for PCT/IL07/00531, mailed Jul. 7, 2008, 2 pages.

Strojnik, P., Acimovic, R., Vavken, E., Simic, V. and Stanic, U. "Treatment of drop foot using an implantable peroneal underknee stimulator." Scandanavian J. of Rehabil. Med. 19:37-43, 1987.

Kralj, A.R. & Bajd, T., "Functional Electrical Stimulation: Standing and Walking after Spinal Cord Injury," CRC Press, Boca Raton, FL., pp. 1-15, 1989.

Final Office Action for U.S. Appl. No. 11/380,430, mailed Nov. 13, 2009.

International Search Report for PCT/IL06/01326, mailed Oct. 13, 2009.

Office Action for U.S. Appl. No. 11/380,430, mailed Mar. 24, 2010.

Office Action for Canadian Application No. 2,632,196, mailed on Mar. 16, 2010.

Examination Report for Australian Application No. 2006314072, mailed on May 5, 2010.

Office Action for U.S. Appl. No. 12/630,199, mailed Jun. 21, 2011.

International Search Report and Written Opinion for International Application No. PCT/US2010/058483, mailed Feb. 7, 2011.

Examination Report for Australian Application No. 2006314072, mailed on Jul. 5, 2011.

Non-Final Office Action for U.S. Appl. No. 11/380,430 mailed Mar. 5, 2009.

Examination Report for European Application No. 07736271.3, mailed on Nov. 14, 2011.

Notice of Reasons for Rejection for Japanese Patent Application No. 2009-517597, mailed Jan. 23, 2012.

Office Action for U.S. Appl. No. 12/631,095, mailed Sep. 14, 2011.

Ness H200 Product Specifications "H200™ Overview& Product Specifications," [online] 2006 [retrieved on Jun. 5, 2007]. Retrieved from the Internet: URL: <http://www.bionessinc.com/products/h200/htm>.

Wood, D.E., "Spatial sensitivity comparisons between an implanted and surface dropped foot neuromuscular stimulator," 9th Annual Conference of the International FES Society, Sep. 2004.

Stralka, "Gait Training (by Stimulating Dorsiflexors)," NM III™ Neuromuscular Stimulation System Suggested Protocol, NM III Program Set #2 Program F, Rehabilicare® 920080 Rev. C.

Neurodan "ActiGait® An implantable drop foot correction system," Neurodan A/S—Products—ActiGait® [online] [retrieved on Jun. 5, 2007]. Retrieved from the Internet: URL: <http://www.neurodan.com/actigait.asp>.

NDI Medical "About ODFS Dropped Foot Stimulator," [online] 2005 [retrieved on Jun. 5, 2006]. Retrieved from the Internet: URL: <http://www.odfs.com/About_ODFS/about_odfs.html>.

NMES Guidelines for Treatment "Gait Training," [online] [retrieved on May 30, 2007]. Retrieved from the Internet: URL: http://www.empi.com/products1nmes/gait.pdf.

Waters, R.L. et al., "Experimental correction of footdrop by electrical stimulation of the peroneal nerve," J Bone Joint Surg Am., vol. 38, No. 8 (Dec. 1975), pp. 1047-1054.

Sowerbutt, C., "Restoring Gait in Stroke Patients Using Functional Neuromuscular Stimulation," [online] Sep. 1, 2006 [retrieved on May 30, 2007]. Retrieved from the Internet: URL: <http://appneurology.com/showArticle.jhtml?print=true&articleID=193104432>.

Office Action for U.S. Appl. No. 11/380,430, mailed Sep. 1, 2010.

Office Action for U.S. Appl. No. 13/036,256, mailed Apr. 5, 2012.

\* cited by examiner

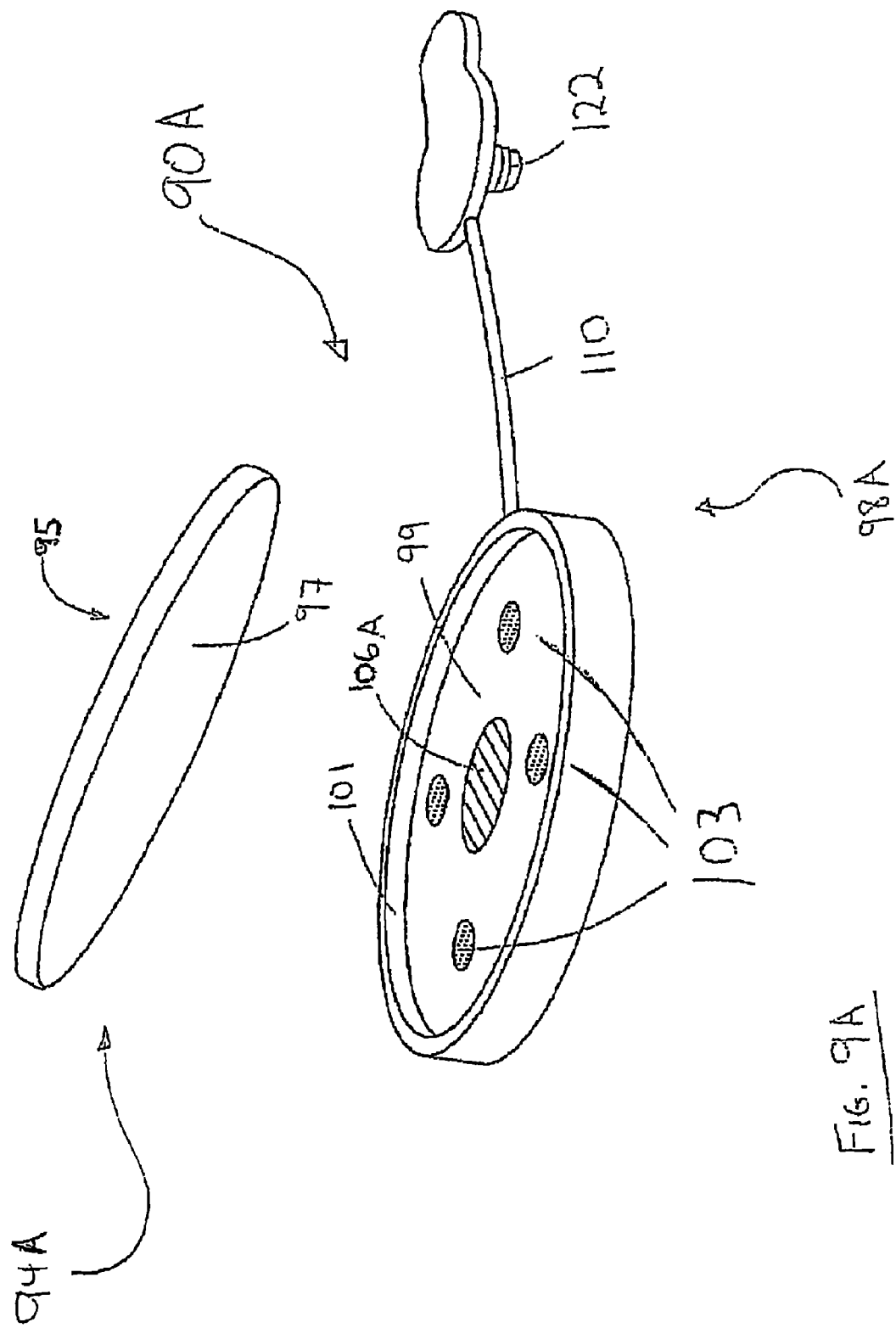

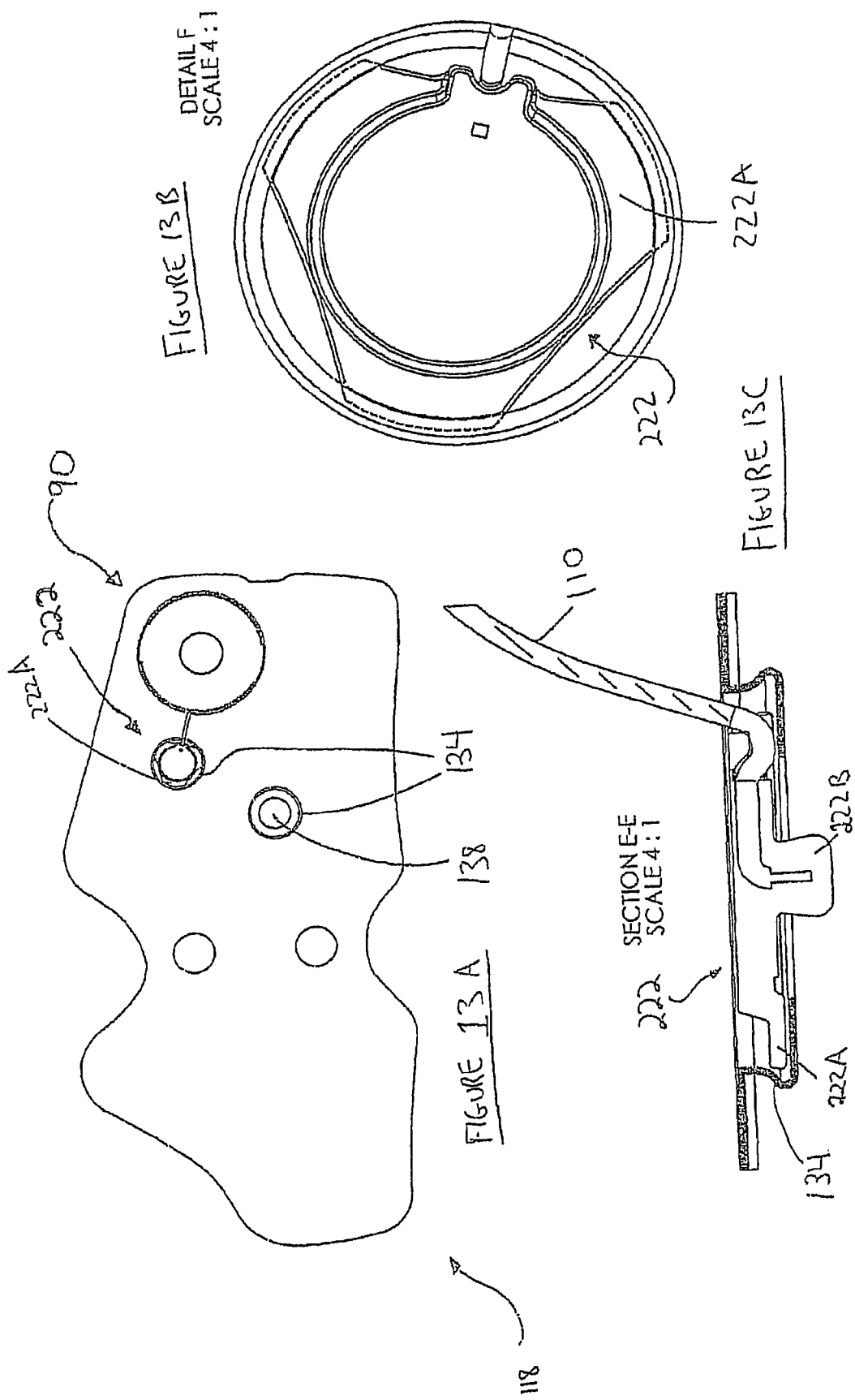

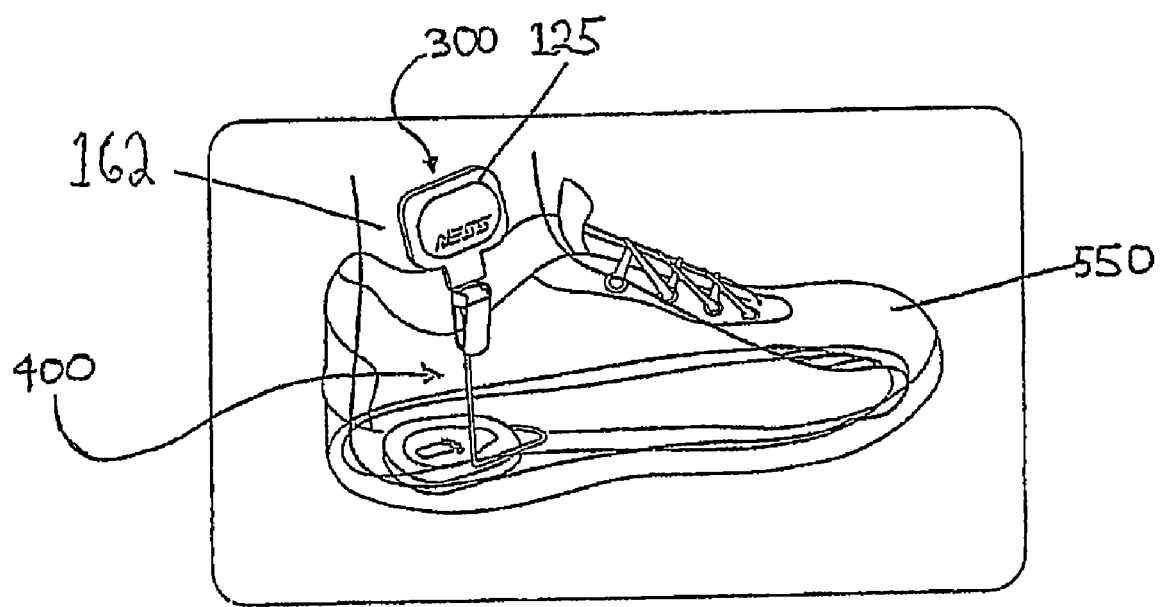
FIGURE 19.a

GAIT MODULATION SYSTEM AND METHOD

CROSS-REFERENCE TO RELATED APPLICATIONS

This application is the U.S. national phase application of International Application No. PCT/IL2006/001326, filed Nov. 16, 2006, entitled "Gait Modulation System and Method," which claims the benefit of priority from U.S. Provisional Application Ser. No. 60/736,858, entitled "Hybrid Orthosis; Foot Sensor; Electrode," filed Nov. 16, 2005, U.S. Non-Provisional Patent Application Ser. No. 11/380,430 (now U.S. Pat. No. 7,899,556), entitled "Orthosis for a Gait Modulation System," filed Apr. 27, 2006, and U.S. Non-Provisional Patent Application Ser. No. 11/552,997 (now U.S. Pat. No. 7,632,239), entitled "Sensor Device for Gait Enhancement," filed Oct. 26, 2006. U.S. Non-Provisional Patent Application Ser. No. 11/552,997 (now U.S. Pat. No. 7,632,239) claims priority to U.S. Provisional Application Ser. No. 60/736,858, entitled "Hybrid Orthosis; Foot Sensor; Electrode," filed Nov. 16, 2005, U.S. Provisional Application Ser. No. 60/746,060, entitled "Foot Sensor Dynamic Gait Tracking Algorithm," filed May 1, 2006, and U.S. Provisional Application Ser. No. 60/805,359, entitled "Foot Sensor Envelope," filed Jun. 21, 2006.

FIELD AND BACKGROUND OF THE INVENTION

The present invention relates to gait modulation systems and methods therefor, and more particularly, to a functional electrical stimulation (FES) orthosis device and a sensor device for such gait modulation systems, and to method of using such devices.

It is known that pathologies of the neuromuscular system due to disease or trauma to the central nervous system, such as stroke, spinal cord injury, head injury, cerebral palsy and multiple sclerosis, can impede proper limb functioning of the hands or legs. Gait, the biomechanical description of walking, can suffer static and dynamic parameter variations due to neuromuscular impairments, which cause non-symmetrical walking, reduced walking speed and reduced walking stability.

Drop foot describes the gait attributable to weak or uncoordinated activation of the ankle dorsi-flexors due to disease or trauma to the central nervous system. Patients suffering from drop foot tend to drag the foot during the swing phase of walking and usually try to compensate for this dragging by hiking their hip or swinging it in a circular motion. These patients tend to have impaired stability, are prone to frequent falls, and their walking movements are unaesthetic and energy consuming.

However, limb muscles can generally be activated with FES. In FES, precisely timed bursts of short electrical pulses are applied to motor nerves, to generate muscle contraction, which can be applied to enhancing limb function.

Although more than four decades have elapsed since the first neuroprosthetic system was proposed, much room remains for improving the technological quality of such systems. This is reflected, inter alia, by the relatively small percentage of potential users who regularly don a neuroprosthetic device to compensate for limb and gait problems, and particularly, a drop foot problem. These systems suffer from many drawbacks that prevent them from being widely used by potential patients.

When problems with arm movement or gait result from stroke or brain injury, they are often accompanied by hand impairment on the same side of the body as the limb on which the FES orthosis is donned. Thus, the donning action must often be carried out using solely the contra-lateral, unaffected hand. Moreover, the posture of the plegic limb is often problematic, especially in cases where spasticity results in reduced voluntary movements and also in a limited passive range of motion of the limb joints. Consequently, objective biomechanical problems exist in donning the orthotic device and in locating the electrodes in exact position onto the limb. Prior art neuroprosthetic devices differ in that they fail to enable facile, quick and accurate donning of the device by an impaired patient using a single hand, and particularly, when even that hand is shaky or otherwise unstable.

Prior art external FES devices typically utilize a stimulator unit that is physically separate from the FES orthosis, to create and control the electrical pulses being applied to motor nerves. The external stimulator unit, which is connected to the FES electrodes by several electrical wires, is located on the body of the user, and is typically attached to the belt of the user. These devices can be inconvenient for the user. Particularly cumbersome is the wiring, which is usually arranged to run along the leg under the clothing to connect the device components.

In addition, neuroprostheses require precise fitting for each individual patient, in an optimal fashion, by exactly identifying the stimulation points that cause contraction of the muscles and positioning and locking the electrodes thereto. Consequently, use of the known devices, which are configured and dedicated to the anatomy and needs of a particular individual, is limited to that individual only, and further requires considerable expertise to reconfigure the device for transfer to another patient.

U.S. Pat. Nos. 5,643,332 and 5,814,093 to Stein disclose an assembly for functional electrical stimulation during movement, including a band, mountable on the leg, carrying all of the components of the assembly to provide a self-contained unit. The components include: electrodes for stimulating a leg nerve; a V-shaped plate for conforming with the leg's tibia to reproducibly position the band so that the electrodes are located over the nerve; a tilt sensor for measuring the angular position of the lower leg; a control circuit for processing the sensor signal information and emitting pulses through the electrodes to stimulate the leg in response to phases of body movement and a battery for supplying power to the tilt sensor, control circuit and stimulator. The disclosed band is made of stretchable, breathable material.

WalkAide™ is a commercially available FES device of Innovative Neurotronics, Inc., and is based on the technology disclosed by Stein. The orthosis component of the WalkAide™ is a narrow band made of a thermoplastic material that is molded to the limb anatomy of an individual user by heating and softening the thermoplastic material and subsequently fitting the contour to the contour of the underlying limb segment. Thus the shape and size of the device and the electrode positioning is custom-fitted to the leg of one user and individualized for the user. This procedure is carried out by a trained medical professional.

For a clinic or rehabilitation center serving a large number of users, it would be advantageous a device that can be transferred from patient to patient hygienically and with facility. Neuroprosthetic devices require a significant and time-consuming set-up procedure carried out by a trained medical professional to fit the device to the anatomy of the limb, position the electrodes accurately over the motor point, and adjust the stimulation parameters when transferring the device to another patient. Parts of the orthosis are in prolonged contact with the skin during a session of use, and existing devices have no provision for hygienically passing the orthosis from the leg of one patient on to another.

Prior art orthosis-based devices for the leg such as the WalkAide™ device operate with relatively small electrodes typically having a diameter of 25-30 mm and a surface area in contact with the skin of no more than about 5-7 $cm^2$ positioned relatively close together in the orthosis. This enables the orthosis to take the form of a relatively narrow band to accommodate the small electrodes and separation. However, activation of the leg muscles by electrical stimulation requires typically high stimulation currents. But the stimulation current passing through the electrode to the skin surface activates skin sensory receptors in addition to underlying excitable motor nerve and muscle tissue and the intensity of sensory activation will depend on the intensity of the current density passing through the skin surface. The level of muscle activation is often limited in the typical patient by his individual tolerance to activation of these skin pain sensors. For these patients, it would be advantageous to reduce the sensory discomfort by lowering the skin current density while maintaining levels of muscle activation. A further means to increase the contraction force of the activated muscles is to increase the distance separating the electrodes in the pair, particularly the distance along the length of the leg. This can result in the recruitment of more muscle fibers, resulting in increased activated rotation torque output from the ankle joint, without the necessity to use a high stimulation current intensity. This electrode geometry and arrangement for increasing muscle force output and reducing sensory discomfort is too large to fit within the prior art narrow band design of the orthosis. To date, no orthosis exists for accommodating surface electrodes of such size and configuration.

Furthermore, a means for accurately positioning the electrodes along the length of the leg becomes essential where the electrodes are significantly separated in this longitudinal direction, and accurate longitudinal positioning of the orthosis becomes mandatory to avoid activating unwanted muscles. Accommodating the large stimulation electrodes with a larger distance separating them particularly in the longitudinal direction requires housing these electrodes in an orthosis that is significantly wider, extending both proximally and distally along the length of the leg. The wide orthosis design introduces new problems concerned with fitting and self-placement. Moreover, the larger dimensions of the orthosis appreciably compromise the ability of the orthosis to fit the contour of the limb segment, especially during limb extensions, flexions and gait.

Some commercially available FES devices utilize a sensor, for disposing underneath the foot of the user, to trigger the electrical pulses being applied to the motor nerves. The sensor senses foot rise or foot strike and accordingly triggers the stimulation pulses administered to the motor nerves. The sensor device is physically distinct from the orthosis.

U.S. Pat. No. 6,507,757 to Swain, et al., discloses one typical foot sensor device of the prior art, in which a foot pressure switch, or sensor, is permanently disposed in the shoe of the affected leg. An electrical circuit is interrupted during the stance phase, when a significant weight is placed on the heel, and reconnects when the heel is lifted during the swing phase. Wires disposed under the clothing connect the sensor with an external stimulator unit that can be attached to the belt or kept in a pocket of the user. The stimulator unit is connected to the electrodes by additional electrical wires.

In other FES orthotic devices, the cumbersome wires are obviated by using a radio frequency (RF) system in which the foot sensor device and other components of the FES orthotic device communicate in a wireless fashion. However, the use of such an RF system necessitates integrating an RF transmitting unit, or head, within the foot sensor device. The transmitting unit can be bulky and sensitive to humidity and mechanical stress. Consequently, such transmitting units are typically mounted on and attached to the calf of the patient.

U.S. Pat. No. D494,273 to Haugland, et al., assigned to Neurodan A/S, describes a pressure sensor switch device for placing underneath the foot of the patient. The communication head is held at a predetermined distance from the sensor device by a wide, semi-rigid spine. The device disclosed by Haugland, et al., can be used as a component of the ActiGait® system manufactured by Neurodan A/S. In the ActiGait® system, the pressure sensor device is inserted into a small pouch within a sock, such that upon donning of the sock, the pressure switch is disposed underneath the foot. A substantially non-elastic band is tightened around the calf to secure the RF unit in place against the calf of the impaired leg.

This approach is disadvantageous in that the patient, who is often hemi-plegic or may suffer from other disorders, is required to add the donning of an additional item—the sock—to his routine. This unintuitive action is particularly problematic for patients who need or prefer to don the FES orthotic device in an unassisted fashion.

A further disadvantage of this design is that the semi-rigid spine may rub against the foot and heel. Also, the electronic head that houses the RF transceiving unit may rub the ankle or lower calf of the user during the course of gait. Moreover, because the pressure switch and RF transceiving unit are mechanically connected by a wide, at least semi-rigid neck, pressures exerted on the electronic head (e.g., when the head gets caught on, or bumped by, an object during the course of gait), are mechanically translated into forces on the foot sensor. These forces may impede the efficacy and sensitivity of the foot sensor. A further disadvantage lies in the limited ability to adjust the electronic head of the pressure switch to different shoe heights: the electronic head protrudes excessively from low-rimmed shoes, and cannot be fitted to shoes or boots in which the rim is at or above the height of the electronic head.

There is therefore a recognized need for, and it would be highly advantageous to have, a sensor device for neuroprosthetic gait enhancement that overcomes the various deficiencies of the prior art devices. It would be of particular advantage to have such a sensor device that is essentially effortless to don, avoids the discomfort associated with prior art sensor devices, and is secured so as to operate in a safe and robust fashion.

It would also be highly advantageous to have an improved FES orthosis for a neuroprosthetic system and method that overcome the manifest deficiencies of the prior art. It would be advantageous to have an FES leg orthosis that can easily and accurately be donned on the limb by patients also suffering from an impaired hand. It would also be of particular advantage to have an FES leg orthosis in which an even pressure of the electrode surface is maintained during limb extensions, flexions and gait. It would be of further advantage to enable greater ankle torque generation with lessening of skin sensory discomfort at the electrode site by increasing the size and longitudinal separation of the electrodes. It would be of yet further advantage for the FES orthosis to be substantially universally adaptable to the different anthropometric variables of limbs and to electrode positioning needs of a wide variety of users. Finally, it would be advantageous to have an FES orthosis designed and configured such that the on-board stimulation unit does not significantly protrude out-side the profile of the orthosis and does not impede donning and wearing clothing such as trousers over the orthosis. This is of major significance to the stroke patient, who is generally is challenged by donning trousers on to his plegic leg using a single hand, and a protruding device attached to his leg may disable his ability to dress himself independently.

SUMMARY OF THE INVENTION

According to the teachings of the present invention there is provided an orthosis for providing electrical stimulation to a limb segment of a user, including: (a) an at least semi-rigid, self-retaining C-shaped frame, the frame configured to substantially envelop the limb segment, the frame including a first flexible and elongated circumferentially retaining element and at least a first and a second opposing flexible and elongated circumferentially retaining elements disposed on the circumferentially opposite side of the frame, the first retaining element and the first opposing retaining element forming a pair of opposing retaining elements, and (b) at least one surface electrical stimulation electrode for contacting at least one stimulation point on a surface of the limb segment, associated with, and supported by, the frame, the at least one surface electrode for electrically associating, via the frame, with a stimulator unit, so as to provide electrical stimulation, wherein the opposing retaining elements are configured to be radially spring-loaded towards a center of the frame, such that in donning the orthosis around the limb segment, the limb segment applies a counter-pressure from within the frame, against the opposing retaining elements, such that the orthosis is firmly and fixedly self-retained in a pre-determined position on the surface of the limb segment.

According to further features in the described preferred embodiments, all of the flexible and elongated retaining elements are configured to conform to a contour of the surface in a substantially independent fashion, so as to maintain intimate contact with the contour.

According to still further features in the described preferred embodiments, the opposing retaining elements include at least three flexible and elongated circumferentially retaining elements.

According to still further features in the described preferred embodiments, the orthosis further includes: (c) a locking mechanism, associated with the frame, for locking the at least one surface electrical stimulation electrode at the predetermined position on the surface of the limb segment.

According to still further features in the described preferred embodiments, the opposing retaining elements are designed and configured to independently respond, mechanically, to changes in the contour, so as to retain the at least one surface electrical stimulation electrode fixed against the predetermined position on the limb segment and so as to maintain an even pressure against the predetermined position on the surface of the limb segment.

According to still further features in the described preferred embodiments, the semi-rigid frame includes a housing for receiving the stimulator unit.

According to still further features in the described preferred embodiments, the housing is dimensioned to envelop and hold the stimulator unit intimately and flatly against the orthosis.

According to still further features in the described preferred embodiments, the orthosis further includes: (c) the stimulator unit, wherein the stimulator unit is designed and configured to: (i) communicate with a sensor for sensing a physical parameter relating to the limb segment, and (ii) based on a signal relating to the sensor, deliver a stimulation signal to the surface electrode.

According to still further features in the described preferred embodiments, the stimulator unit includes a radio frequency transceiver for communicating with at least one of a stimulator control unit and the sensor.

According to still further features in the described preferred embodiments, the locking mechanism includes at least one elastic strap designed to extend circumferentially around and bridge between the opposite sides of the frame and to be reversibly fastened to a fastening element associated with the frame.

According to still further features in the described preferred embodiments, the orthosis is a lower-leg orthosis, an upper contour of the orthosis is a locating surface, the locating surface configured to conform to an inferior border of a patella of the user.

According to still further features in the described preferred embodiments, the locating surface has a three-dimensional cup shape for abutting an inferior border of a patella of the user during donning of the orthosis.

According to still further features in the described preferred embodiments, the orthosis is adapted for single-handed donning by the user.

According to still further features in the described preferred embodiments, the fastening element includes a protuberance associated with the frame.

According to still further features in the described preferred embodiments, the protuberance includes a housing for receiving the stimulator unit.

According to still further features in the described preferred embodiments, the at least one elastic strap terminates in a looped handle, the looped handle adapted to be reversibly fastened to the fastening element.

According to still further features in the described preferred embodiments, the orthosis further includes: (c) the neuroprosthetic stimulator unit, and (d) a housing for receiving the stimulator unit, the housing disposed on a flexible leaf on the frame, such that the housing and the leaf are free to move as a unit, independently of the retaining elements, so as enable the retaining elements to mechanically respond, substantially independently, to changes in a contour of the leg segment, even when pressure is exerted on an exterior face of the stimulator unit.

According to still further features in the described preferred embodiments, circumferentially disposed on the frame is at least one spring-loaded strip, the strip being radially spring-loaded towards a center of the frame, such that in donning the orthosis around the limb segment, the spring-loaded strip applies a pressure against the limb segment, such that the orthosis is self-retained in position on the limb segment while allowing for small adjustments to be made in positioning of the orthosis on the limb segment.

According to still further features in the described preferred embodiments, the second flexible and elongated circumferentially retaining element has a width, W, wherein W is within a range of about 2-4.5 cm.

According to still further features in the described preferred embodiments, the second opposing retaining element has a width, W, and the orthosis has a height, H, and wherein W is within a range of 8-60% of H.

According to still further features in the described preferred embodiments, each of the at least one surface electrical stimulation electrode has a surface area for contacting the surface of the limb segment, and wherein for each electrode, the surface area is at least 9 cm2.

According to still further features in the described preferred embodiments, the surface area is at least 12 cm2.

According to still further features in the described preferred embodiments, the at least one elastic strap terminates in a looped handle, the looped handle designed to be reversibly fastened to the fastening element, and wherein the looped handle, when fastened to the fastening element, completes a smooth and substantially non-protruding profile that includes the stimulator unit, the housing, and the looped handle, all of which together blend into a profile of a leg of the user.

According to still further features in the described preferred embodiments, the stimulator unit is a neuroprosthetic stimulator unit.

According to another aspect of the present invention there is provided an orthosis for providing electrical stimulation to a limb segment of a user, the orthosis including: (a) an at least semi-rigid frame being configured to substantially envelop the limb segment; (b) a soft inner facing for at least partially covering an inner face of the frame and for providing a comfortable interface between the frame and the limb segment; (c) a first mechanical fitting associated with the inner face of the frame, and (d) at least one surface electrical stimulation electrode assembly associated with, and supported by the frame, the assembly having a stimulation electrode having a first surface for contacting at least one stimulation point on the limb segment, and an attachment mechanism for fixing a position of the electrode with respect to the frame, the at least one surface electrode for electrically associating, by way of the frame, with a stimulator unit for providing a stimulation signal to the surface electrode, and wherein the stimulation electrode assembly has a second mechanical fitting, complementary to the first mechanical fitting, for reversibly attaching the stimulation electrode assembly to, and reversibly detaching the stimulation electrode assembly from, the first mechanical fitting.

According to further features in the described preferred embodiments, the first and second mechanical fittings are connectors selected from the group consisting of snaps and hook and loop fasteners.

According to still further features in the described preferred embodiments, the attachment mechanism includes an electrode base having a surface for receiving and engaging a second surface of the stimulation electrode, the second surface being opposite the first surface.

According to still further features in the described preferred embodiments, the electrode base has a rim for physically defining, for the stimulation electrode, a substantially singular position therein.

According to still further features in the described preferred embodiments, the second surface of the stimulation electrode includes a hydrogel-containing surface, and wherein the surface of the electrode base includes at least one patch of hook fasteners for securing the hydrogel-containing surface to the electrode base.

According to still further features in the described preferred embodiments, the soft inner facing is a reversibly attachable and detachable panel.

According to still further features in the described preferred embodiments, the orthosis further includes: (e) a soft panel for covering at least a portion of the soft inner facing, the soft panel having a third complementary connector for associating with a fourth complementary connector associated with the frame, so as to reversibly secure the soft panel to the frame.

According to still further features in the described preferred embodiments, the attachment mechanism includes an electrode base having a surface for attaching to a second surface of the stimulation electrode, the second surface being opposite the first surface.

According to still further features in the described preferred embodiments, the electrode base has a cover, attached to the base, the cover for protecting a perimeter of the stimulation electrode.

According to still further features in the described preferred embodiments, the cover is adapted so as to leave exposed a majority of the first surface.

According to still further features in the described preferred embodiments, the perimeter includes hydrogel.

According to yet another aspect of the present invention there is provided an orthosis for providing electrical stimulation to a limb segment of a user, the orthosis including: (a) an at least semi-rigid frame configured to substantially envelop the limb segment, the frame having at least one first complementary mechanical fastener associated therewith; (b) at least one surface electrical stimulation electrode assembly associated with, and supported by the frame, the assembly having a surface stimulation electrode for contacting at least one stimulation point on the limb segment, the at least one surface electrode assembly having an electrode base for electrically associating, via the frame, with a stimulator unit for providing a stimulation signal to the surface electrode, the electrode base having a top face for receiving the stimulation electrode, the electrode base having a bottom face having at least one second complementary mechanical fastener, the second fastener being complementary to the first fastener, the first and second fasteners designed and configured for reversible attachment and reversible detachment, at a plurality of locations on the frame, thereby enabling the electrical stimulation electrode assembly to be adjustably and reversibly positioned on the frame.

According to further features in the described preferred embodiments, the electrode base is associated with a conductive element for electrically connecting the base to the stimulator unit.

According to still further features in the described preferred embodiments, the conductive element is a first conductive complementary mechanical fastener, and wherein associated with the frame is a second conductive complementary mechanical fastener, the first conductive fastener being complementary to the second conductive fastener.

According to still further features in the described preferred embodiments, the electrode base is loosely associated with the first conductive fastener by means of a flexible wire, thereby enabling the electrical stimulation electrode assembly to be adjustably and reversibly positioned on the frame in a plurality of positions, according to individual needs of the user.

According to still further features in the described preferred embodiments, the electrode base is associated with the first conductive fastener by means of a flexible wire, thereby substantially decoupling an electrical connection of the electrode assembly to the stimulator unit from a mechanical connection of the electrode assembly to the stimulator unit, so as to enable the electrode assembly to be adjustably and reversibly positioned on the frame in a plurality of positions, according to individual needs of the user.

According to still further features in the described preferred embodiments, the first and second fasteners include hook and loop fasteners.

According to yet another aspect of the present invention there is provided an orthosis for providing electrical stimulation to a limb segment of a user, the orthosis including: (a) a frame configured to substantially envelop a limb segment of a user, the frame being made of an at least semi-rigid material and associated with a first fastener at an inner face of the frame; (b) at least one electrical stimulation electrode assembly associated with, and supported by the frame, the stimulation electrode assembly for electrical association, via the frame, with a stimulator unit; (c) a soft, reversibly attachable and detachable layer having a second fastener complementary to the first fastener for reversible attachment and detachment of the layer from an inner face of the frame, the at least one electrical stimulation electrode assembly being associated with, and located on, an inner face of the layer such that, when the orthosis is donned on the limb segment, an electrical stimulation electrode of the electrode assembly is positioned so as to contact at least one stimulation point of a muscle of the user, the soft, reversibly attachable and detachable layer for providing the user with a comfortable interface between the frame and the limb segment during donning of the orthosis.

According to further features in the described preferred embodiments, the first fastener and second fastener include a hook and loop arrangement.

According to still further features in the described preferred embodiments, the layer further includes a snap connector for attaching the layer to the frame, the snap connector being complementary to a connector associated with the frame so as to provide a secure mechanical attachment to the frame, thereby ensuring exact and repeatable positioning of the layer, with respect to the frame.

According to still further features in the described preferred embodiments, the layer further includes a hollow snap connector, the hollow connector being complementary to a recess associated with the frame so as to provide a tight mechanical attachment to the frame, thereby ensuring exact and repeatable positioning of the layer, with respect to the frame.

According to still further features in the described preferred embodiments, the layer further includes a hole for enabling the electrical association.

According to still further features in the described preferred embodiments, the electrical stimulation electrode assembly includes a connector designed to penetrate the hole and to connect to a complementary connector associated with the frame.

According to still further features in the described preferred embodiments, the reversibly attachable and detachable layer is fully flexible.

According to yet another aspect of the present invention there is provided an orthosis for providing electrical stimulation to a limb segment of a user, the orthosis including: (a) a frame adapted to substantially envelop a limb segment of a user, the frame being made of an at least semi-rigid material and associated with a first fastener at an inner face of the frame; (b) at least one electrical stimulation electrode assembly associated with, and supported by the frame, the stimulation electrode assembly for electrically associating, via the frame, with a stimulator unit, the assembly including an electrical stimulation electrode and a stimulation electrode base; (c) a reversibly attachable and detachable layer having a second fastener complementary to the first fastener for reversible, yet secure mechanical attachment and detachment of the layer to and from an inner face of the frame, the at least one stimulation electrode base being attached to, and located on, an inner face of the layer, such that, when the orthosis is donned on the limb segment, the electrical stimulation electrode is positioned to contact at least one stimulation point of a muscle of the user, and wherein the electrode assembly and the layer are designed and configured so as to enable positioning and securing of the electrode assembly on the layer in a plurality of positions, according to individual needs of the user.

According to further features in the described preferred embodiments, the electrode assembly and the layer are further designed and configured such that the positioning is adjustable and reversible.

According to still further features in the described preferred embodiments, the electrode base has at least a first connector, and the layer has at least a second connector, the second connector being complementary to the first connector, so as to achieve the positioning and securing.

According to still further features in the described preferred embodiments, the electrode assembly and the layer are further designed and configured such that the positioning is adjustable and reversible.

According to still further features in the described preferred embodiments, the electrode base has a loose association with the first connector, so as to enable the positioning and securing of the electrode assembly on the layer in the plurality of positions.

According to still further features in the described preferred embodiments, the loose association is achieved by a flexible wire.

According to still further features in the described preferred embodiments, the reversibly attachable and detachable layer is fully flexible.

According to yet another aspect of the present invention there is provided a method of providing electrical stimulation to a limb segment of a user, the method including the steps of: (a) providing a electrical stimulation device including an electrical stimulation orthosis, the orthosis including: (i) a frame being configured to substantially envelop a limb segment of a user, the frame being made of an at least semi-rigid material and associated with a first fastener at an inner face of the frame; (ii) at least one electrical stimulation electrode associated with, and supported by, the frame, the stimulation electrode being electrically associating, via the frame, with a stimulator unit; (iii) a soft, reversibly attachable and detachable layer having a second fastener complementary to the first fastener for reversibly attaching and detaching the layer from an inner face of the frame, the at least one electrical stimulation electrode being associated with, and located on, an inner face of the layer so as to contact at least one stimulation point of a muscle of the user, and (b) donning the electrical stimulation device on the limb segment.

According to still further features in the described preferred embodiments, the method further includes the step of: (c) reversibly repositioning the electrical stimulation electrode on the inner face of the layer.

According to still further features in the described preferred embodiments, the method further includes the step of: (c) reversibly detaching the layer from the inner face of the frame.

According to yet another aspect of the present invention there is provided an electrode assembly including a surface electrode having: a hydrogel layer having a first face and a second face, the second face substantially opposite the first face, and at least one underlying surface layer, associated with the first face of the hydrogel layer, a supporting surface layer, disposed along the second face, the supporting surface layer attached to the underlying surface layer so as to provide mechanical reinforcement of the hydrogel layer.

According to further features in the described preferred embodiments, the supporting surface layer is adapted to reinforce a perimeter of the hydrogel layer.

According to still further features in the described preferred embodiments, the at least one underlying surface layer includes at least a first layer disposed directly against the hydrogel layer, and a second layer disposed against the first layer, and wherein the second layer is attached to the supporting surface layer.

According to still further features in the described preferred embodiments, the supporting surface layer includes polypropylene.

According to still further features in the described preferred embodiments, the second layer includes polypropylene.

According to still further features in the described preferred embodiments, the second layer includes hook or loop fasteners.

According to still further features in the described preferred embodiments, the supporting surface layer and the underlying surface layer are attached through the hydrogel.

According to still further features in the described preferred embodiments, the supporting surface layer and the underlying surface layer are attached by a glue.

According to still further features in the described preferred embodiments, the supporting surface layer and the underlying surface layer are attached by a weld.

According to still further features in the described preferred embodiments, the supporting surface layer and the underlying surface layer are attached by an ultrasonic weld.

According to still further features in the described preferred embodiments, the second layer includes a non-woven material.

According to still further features in the described preferred embodiments, the supporting surface layer includes a non-woven material.

According to still further features in the described preferred embodiments, the supporting surface layer and the underlying surface layer are attached around a perimeter of the hydrogel.

According to still further features in the described preferred embodiments, the supporting surface layer is substantially ring-shaped.

According to yet another aspect of the present invention there is provided a foot sensor device for gait enhancement, including: (a) a sensor unit having an external casing, the sensor unit for disposing within a shoe of a user, the sensor unit for sensing a parameter associated with a gait event; (b) an electronic communication unit, electrically associated with the sensor unit, for receiving a signal pertaining to the parameter, the electronic unit having: (i) a microcontroller; (ii) a transmitting unit for transmitting, in a wireless fashion, gait information based on the signal, to a unit of the orthosis external to the foot sensor device, and (iii) a housing for housing at least one of the microcontroller and the transmitting unit, and (c) a fastening unit, attached to the housing, the fastening unit adapted to fasten on to the shoe, so as to secure the electronic communication unit in a substantially fixed position during gait of the user.

According to still further features in the described preferred embodiments, the fastening unit includes a clamp unit.

According to still further features in the described preferred embodiments, the fastening unit is adapted to fasten on to a rim of the shoe.

According to still further features in the described preferred embodiments, the clamp unit has at least two arms designed and configured to fasten around a rim of the shoe.

According to still further features in the described preferred embodiments, the clamp unit is at least semi-rigidly associated with the housing.

According to still further features in the described preferred embodiments, the clamp unit is rigidly associated with the housing.

According to still further features in the described preferred embodiments, the housing of the electronic unit and the casing of the sensor unit are substantially mechanically independent.

According to still further features in the described preferred embodiments, the clamp unit further includes a locking lever adapted for locking the arms in position around the rim of the shoe.

According to still further features in the described preferred embodiments, a facing of the housing is concave, so as to fit a natural curvature of a leg of the user.

According to still further features in the described preferred embodiments, the housing and the clamp unit each have a face for disposing towards a leg of the user when the user wears the shoe, the device being designed and configured such that the housing and the clamp unit are attached to form an angle within a range of about 150° to about 175° between the faces.

According to still further features in the described preferred embodiments, the angle is in a range of about 155° to about 175°.

According to still further features in the described preferred embodiments, the angle is in a range of about 160° to about 175°.

According to still further features in the described preferred embodiments, the angle is in a range of about 160° to about 170°.

According to still further features in the described preferred embodiments, the transmitting unit is a transceiving unit.

According to still further features in the described preferred embodiments, the foot sensor device further includes: (d) the shoe.

According to still further features in the described preferred embodiments, the sensor unit is disposed under an inner sole of the shoe.

According to still further features in the described preferred embodiments, the fastening unit includes a clamp unit adapted to enable a hemiplegic patient to affix the clamp unit to the shoe, using a single hand.

According to yet another aspect of the present invention there is provided a method of enhancing gait, including the steps of: (a) providing a device including: (i) a sensor unit having an external casing, the sensor unit for disposing within a shoe of a user, the sensor unit for sensing a parameter associated with a gait event; (ii) an electronic communication unit, electrically associated with the sensor unit, for receiving a signal pertaining to the parameter, the electronic unit having: (A) a microcontroller; (B) a transmitting unit for transmitting, in a wireless fashion, gait information based on the signal, to a unit of the orthosis external to the foot sensor device, and (C) a housing for housing at least one of the microcontroller and the transmitting unit, and (iii) a fastening unit, attached to the housing, the fastening unit adapted to fasten on the shoe, so as to secure the electronic communication unit in a substantially fixed position during gait of the user, and (b) donning the device by affixing the fastening unit to the shoe.

According to still further features in the described preferred embodiments, the affixing of the fastening unit includes affixing of a clamp unit.

According to still further features in the described preferred embodiments, the fastening unit is affixed to a rim of the shoe.

According to still further features in the described preferred embodiments, the clamp unit has at least two arms that fasten around a rim of the shoe.

According to still further features in the described preferred embodiments, the housing of the electronic unit and the casing of the sensor unit are substantially mechanically independent.

According to still further features in the described preferred embodiments, the method of claim 95, further including, prior to step (b), the step of: (c) disposing the sensor unit under an inner sole of the shoe.

According to still further features in the described preferred embodiments, the affixing of the fastening unit is effected using a single hand.

According to still further features in the described preferred embodiments, the affixing of the fastening unit is effected using a single hand.

According to still further features in the described preferred embodiments, the affixing of the fastening unit is effected by a hemiplegic patient using a single hand.

According to still further features in the described preferred embodiments, the method further includes the step of: (c) locking the arms in position against the rim of the shoe.

According to yet another aspect of the present invention there is provided a method of configuring operating parameters of an electrical stimulation orthosis system, including the steps of: (a) providing a personal digital assistant including: (i) a central processing unit having a memory; (ii) an input device; (iii) an operating system interfacing between the input device and the central processing unit, and (iv) configuration software, for configuration of the orthosis system, having specific interface for producing the configuration commands; (b) providing a control unit for controlling the electrical stimulation orthosis, and (c) providing a housing having at least one receptacle for receiving the personal digital assistant and the control unit, the housing adapted to electrically connect between the personal digital assistant and the control unit, (d) inserting the personal digital assistant and the control unit into the housing, so as to electrically connect between the personal digital assistant and the control unit; (e) attaching the electrical stimulation orthosis to a limb of a user, (f) activating the electrical stimulation orthosis so as to effect stimulation of the limb, and, while the personal digital assistant and the control unit are electrically connected in the housing, (g) monitoring at least one operating parameter associated with the electrical stimulation orthosis system, using the personal digital assistant, and (h) providing configuration commands, by the personal digital assistant, via the control unit, so as to configure the electrical stimulation orthosis, such that the control unit transmits the configuration commands and monitors operating parameters from the electrical stimulation orthosis system, during the stimulation of the limb.

According to still further features in the described preferred embodiments, the at least one operating parameter includes a stimulation profile.

According to still further features in the described preferred embodiments, the at least one operating parameter includes stimulation synchronization.

According to still further features in the described preferred embodiments, the at least one operating parameter includes user history of the user.

According to still further features in the described preferred embodiments, the user history includes at least one previous configuration associated with the user.

According to still further features in the described preferred embodiments, the user history includes an amount of use of the system by the user.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 9A is a perspective view of another embodiment of the inventive electrode assembly;

FIG. 13A is a schematic perspective view of the electrode assembly and detachable layer, according to another embodiment of the present invention;

FIG. 13B is a detailed magnification of FIG. 13A;

FIG. 13C is a detailed, magnified, cross-sectional view of a snap connector of the electrode assembly mechanically connected to a complementary connector on the detachable layer;

FIG. 19a is a schematic, three-dimensional view of the inventive foot sensor device mounted on the shoe rim, with the communication head hugging the inner calf of the user;

FIG. 19b is a schematic, three-dimensional top view of FIG. 19a, and

DESCRIPTION OF THE PREFERRED EMBODIMENTS

Figure 1:
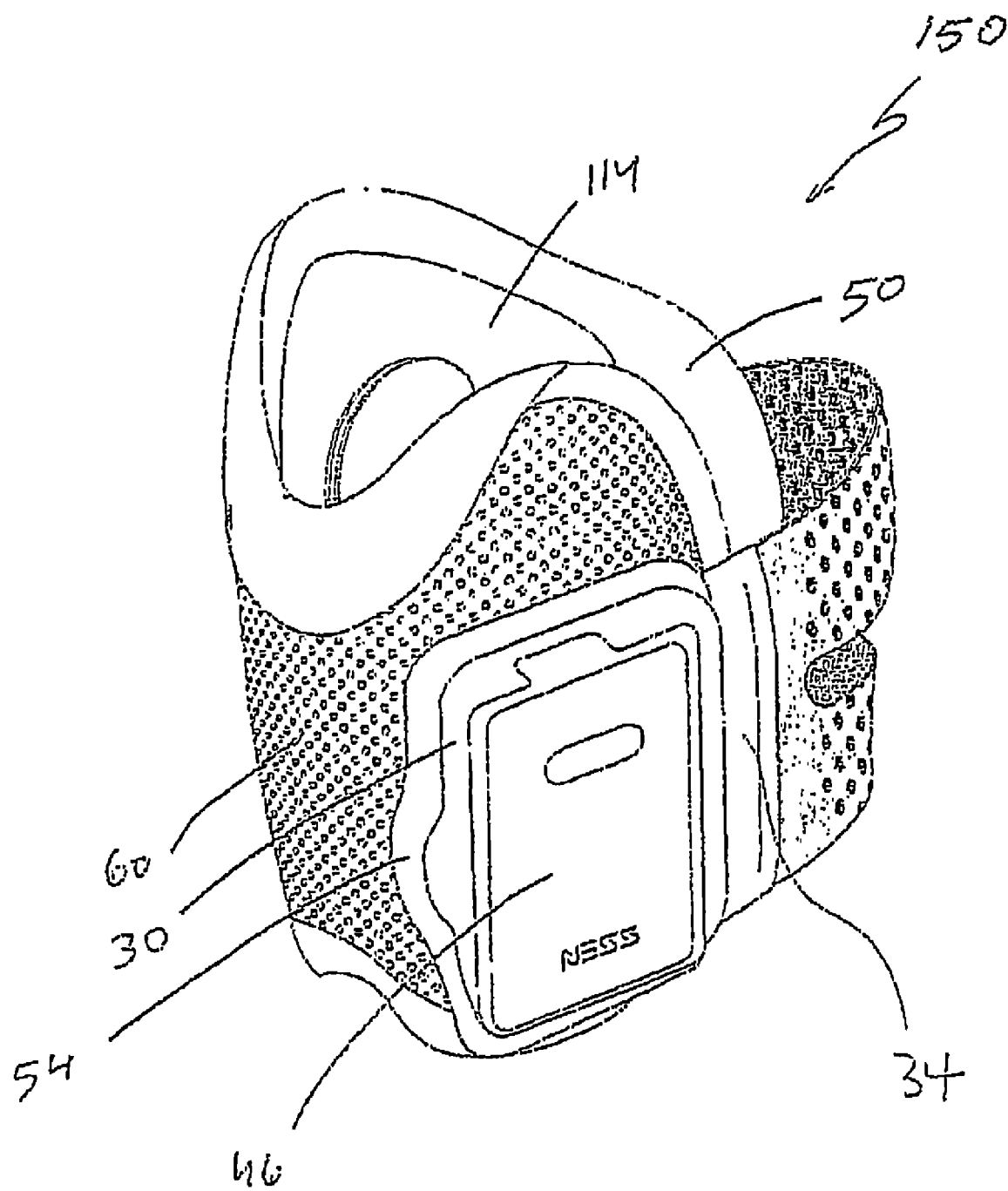
FIG. 1 is a perspective view of the inventive FES orthosis for gait modulation.

One aspect of the present invention is an improved electrical stimulation orthosis and method, and more particularly, a functional electrical stimulation (FES) orthosis for users suffering from gait problems such as drop foot. The orthosis can easily be donned on the leg, even by patients suffering from an impaired hand.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Figure 2:
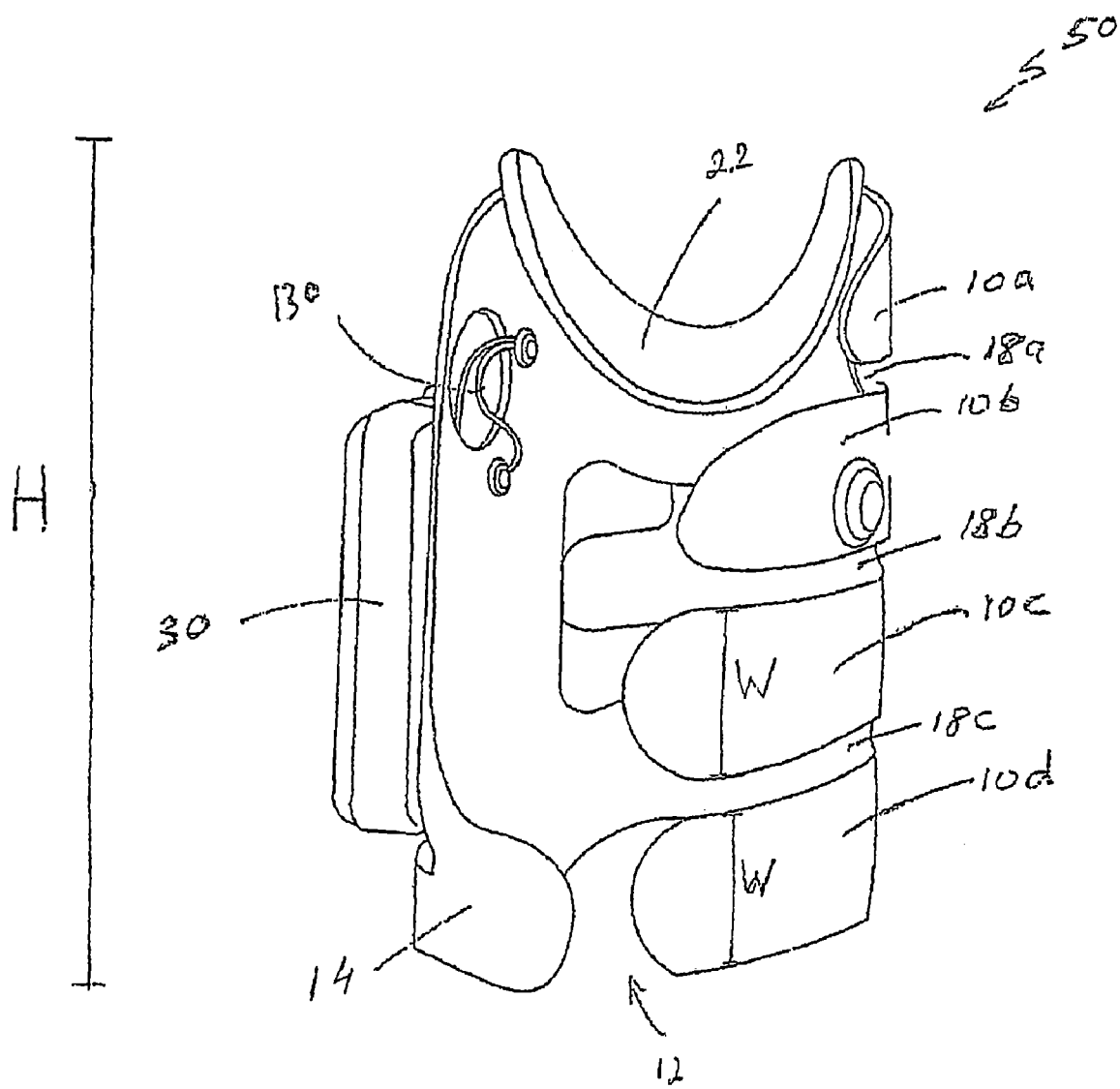
FIG. 2 is a perspective front view of a central, semi-rigid frame of the inventive FES orthosis of FIG. 1.
Figure 3:
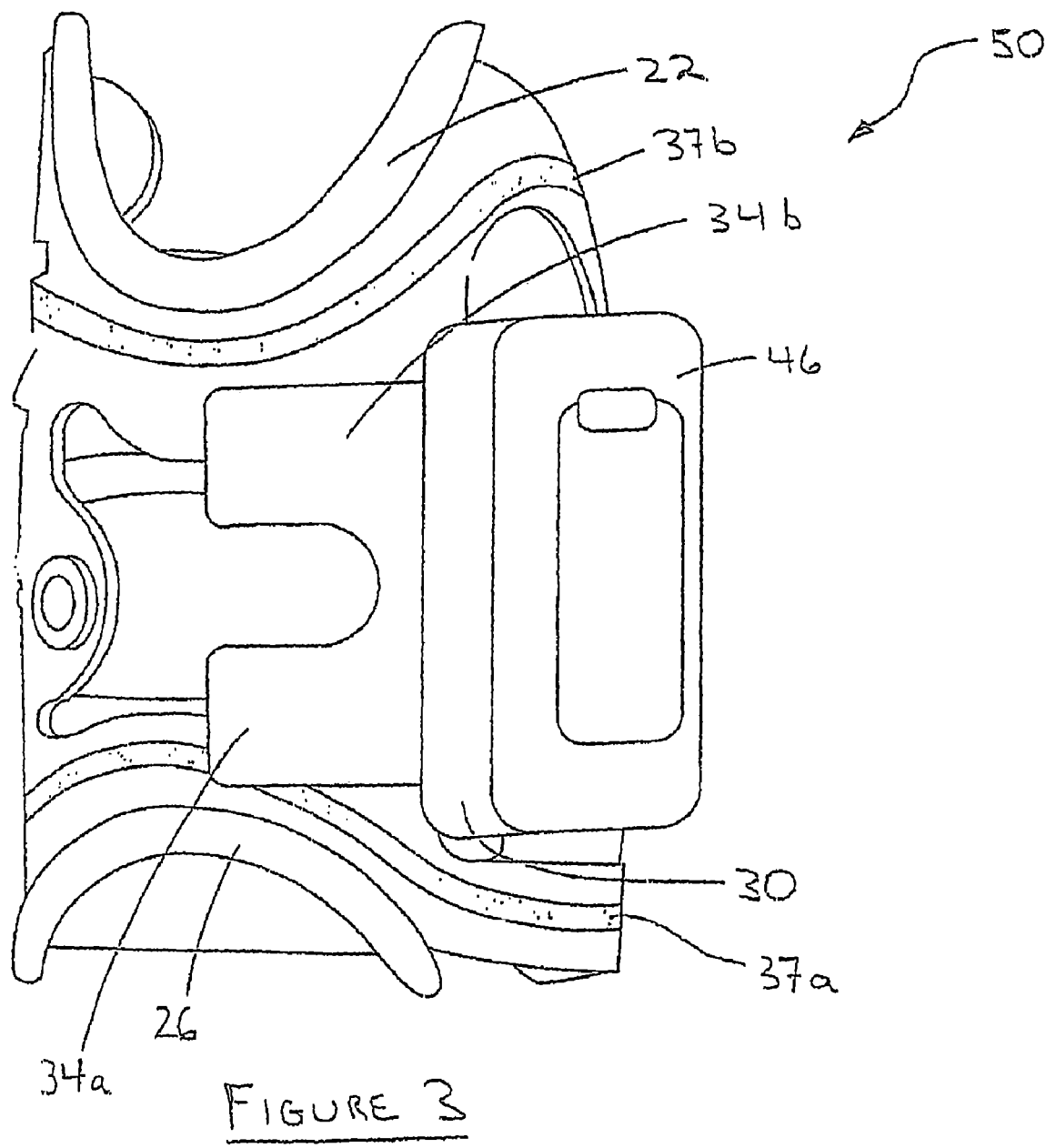
FIG. 3 is a perspective back view of the frame of FIG. 2, showing also an attached stimulator unit and housing.

Referring now to the drawings, FIG. 1 is a perspective view of the inventive FES gait modulation orthosis 150; FIG. 2 and FIG. 3 are perspective front and back views, respectively, of the central, semi-rigid frame 50 of the FES orthosis. It can be seen from these drawings that FES orthosis 150 includes three layers: central frame 50, which is at least semi-rigid, an internal soft layer 114 covering the inner facing of frame 50, and an external soft layer 60 covering the outer facing of frame 50. Additionally, orthosis 150 includes a neuroprosthetic stimulation unit 46, as well as stimulation electrode assemblies (shown in detail in FIG. 9 and described hereinbelow).

As used herein in the specification and in the claims section that follows, the term "limb segment" refers to a limb segment including a portion of the upper or lower arm, or the upper or lower leg.

As used herein in the specification and in the claims section that follows, the term "envelop", "enveloping", and the like, with regard to a limb segment and an article therefor, refers to an article that substantially surrounds and covers at least one half the circumference of a limb segment.

As used herein in the specification and in the claims section that follows, the term "reversible", "reversibly", and the like, with respect to attachment and/or detachment of an element or assembly, refers to a non-destructive, repeatable attachment and/or detachment. The term "reversible attachment", "reversibly attached", and the like, with respect to a soft layer associated with the frame of the orthosis, further refers to a reproducible positioning of the soft layer, with respect to the frame, each time the soft layer is reattached.

As used herein in the specification and in the claims section that follows, the term "inner face" refers to at least one of: the face of the detachable layer for contacting the surface of the limb segment of the user, and the face of the soft inner layer disposed within the central frame. Thus, in an orthosis in which there is no detachable layer, the term "inner face" refers to the face of the soft inner layer disposed within the central frame.

As used herein in the specification and in the claims section that follows, the term "fully flexible", with respect to the detachable layer, refers to a layer that is not self-supporting.

Central frame 50 is ergonomically configured to at least partially envelop the limb segment, more preferably, to surround at least ⅔ of the circumference of the limb segment, and most preferably, to substantially envelop the limb segment completely. As shown in FIG. 2, frame 50 includes at least one circumferentially retaining element pair 12 for tightly enveloping the limb. Retaining element pair 12 includes opposing, flexible and elongated members, such as flexible, elongated member 14 and flexible, elongated member 10c. Preferably, retaining element pair 12 includes flexible and elongated members that are substantially directly opposite, such as member 14 and member 10d.

In addition, flexible, elongated members 14, 10a-d are flexible, and spring-loaded towards the limb segment. Hence, in increasing the diameter of central frame 50, the pressure applied from within frame 50 must overcome the resistance of the spring-loaded retaining element pair 12, as well as the resistance of additional flexible and elongated members 10a-10c. Consequently, when orthosis 150 is donned by expanding frame 50 around the limb segment, orthosis 150 is tightly held in the desired position by retaining element pair 12 and additional members 10a-10c.

Preferably, spring-loaded metal strips 37a, 37b are disposed around the circumference of frame 50, to augment the spring-loading action of flexible, elongated members 14, 10a-d, and to maintain the efficacy of the spring-loading action over the lifetime of orthosis 150.

Central frame 50 is preferably configured to have one individual elongated member 14 on a first side of retaining element pair 12, and two to four individual elongated members 10a to 10d on the opposing side, more preferably, three elongated members, and most preferably, at least four, as shown in FIGS. 2 and 3. In this case, frame 50 resembles an open hand where individual retaining members 10a to 10d resemble fingers, and individual retaining member 14 resembles a thumb.

While inventive FES orthosis 150 can be designed to have two or more individual retaining member on each side, the inventors have found that having a single, narrow retaining member (such as retaining member 14) on one of the sides facilitates both the donning process and the doffing process. Preferably, each single, narrow retaining member 14, 10a-d has a width of 1.0-6 cm, more preferably, 2-4.5 cm, and most preferably, 2.5-3.5 cm. Within these width ranges, this single, narrow retaining member is wide enough to grip the limb segment, and narrow enough to enable facile donning of the orthotic device. With respect to the height of the orthotic device, the single, narrow retaining member has a width W within a range of 8-60% of the height of the orthotic device, more preferably, 10-35%, and most preferably, 15-30%. Above these ranges, central frame 50 acts in a more rigid fashion during the donning process and the doffing process.

Disposed between retaining members 10a to 10d are gaps 18a to 18c, as shown in FIG. 2. Gaps 18a to 18c enable elongated members 10a-10d to conform in substantially independent fashion to the contours of the limb segment, both when the limb segment is static and dynamic. It should be emphasized that various limb segments exhibit large profile changes, especially during articulations of the neighboring joints, along with activation of the muscles of the particular limb segment.

Thus, the above-described arrangement enables a superior enveloping of the limb segment by frame 50, and serves to effectively disperse the pressure and strains on the limb tissue, retaining thereby the natural profile and geometry of the limb tissue and muscles. The dispersion of pressures via flexible members 10a to 10d also enables an orthosis 150 of a particular diameter and contour to accommodate a wide variety of limb diameters and profiles.

Significantly, the open-hand shape of central semi-rigid frame 50 also allows the limb to be firmly gripped and retained in exact position by FES orthosis 150 during donning of the device, until final locking of orthosis 150, which will be described hereinbelow.

When FES orthosis 150 is donned on a leg, the above-described arrangement is particularly suitable for enabling the orthosis to adapt to anatomical changes with time, as well as to changes due to the contraction and expansion of the muscles during walking, while maintaining the stimulation electrode in accurate position against the contact points on the leg segment, and with even pressure.

Figure 3A:
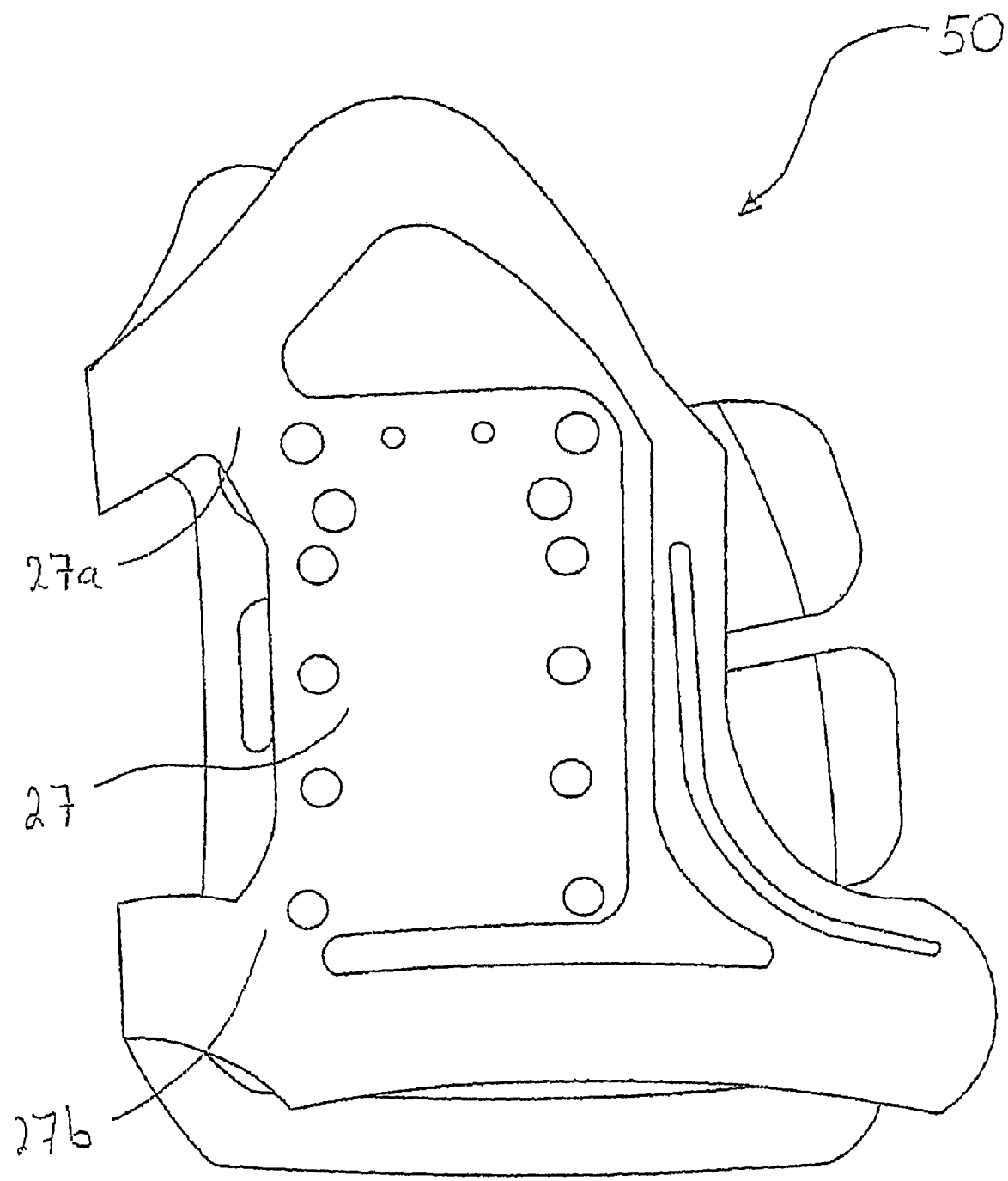
FIG. 3A is a perspective side view of the frame of the FES orthosis of FIG. 2, with the stimulator unit and housing removed to reveal a flexible leaf, integral to the frame, for supporting the stimulator unit housing.

FIG. 3A is a perspective side view of central frame 50, revealing a flexible leaf or plate 27, integral to frame 50, for supporting the stimulator unit housing or cradle 30 (not shown). Flexible leaf 27 is preferably attached to frame 50 solely on one side (or on a portion of one side), such that pressure exerted on stimulation unit 46 (not shown) is substantially absorbed solely by flexible leaf 27. This enables the surface electrical stimulation electrodes to maintain a fixed position, and with substantially even pressure, against a predetermined position on the surface of the limb segment, even when stimulation unit 46 is knocked, pushed, or pulled. In FIG. 3A, flexible leaf 27 is connected to frame 50 solely by two narrow necks 27a, b, so as to minimize pressures and strains on frame 50 due to stimulation unit 46.

When suitably positioned below the knee, (see also FIGS. 5 and 6), orthosis 150 provides electrical stimulation to the contact points overlying the Peroneal nerve and the Tibialis Anterior, Peroneus Longus, Extensor Digitorum Longus or extensor Hallucis Longus muscles, so as to modulate the gait. To guide the positioning, central frame 50 preferably includes an upper locator 22, and a lower locator 26. Upper locator 22 preferably has the form of a three-dimensional inverted arch, contoured, so as to conform to the inferior border of the tuberosity of the patella and to the characteristic anatomical recesses on each side thereof. The edge of the device is made of elastomeric material to provide comfort when positioned on the limb, and to improve the stability of FES orthosis 150 on the limb segment.

Upper locator 22 includes a molding extending from semi-rigid frame 50 so as to abut the inferior border of the patella, while lower locator 26 is designed to conform to the characteristic anatomical shape of the inferior surface of the tibial crest. When donning FES orthosis 150 on the leg, locator 22 assists both in the accurate longitudinal placement of orthosis 150 along the long axis of the lower leg segment, and in the rotational orientation about the long axis of the leg segment, as will be described in greater detail hereinbelow. Locator 26 assists in the rotational orientation about the long axis of the leg segment.

After exact positioning of FES orthosis 150 on the stimulation points has been achieved, orthosis 150 is firmly secured and locked on to the limb segment by a robust fastening arrangement 34 (shown in FIGS. 1 and 3), which is firmly associated at a first end, with central frame 50, and ends in a handle 54 at the opposite end. Fastening arrangement 34 further includes substantially parallel, elastic modular straps 34a and 34b, connecting between the first end and handle 54. Elastic modular straps 34a and 34b are designed such that during donning, straps 34a and 34b wrap circumferentially around the limb segment, to tightly lock FES orthosis 150 in place around the segment. The locking may be effected by fastening handle 54 to stimulator unit housing or cradle 30. Various exemplary alternatives for this fastening are provided hereinbelow.

Each of elastic straps 34a and 34b is equipped with an adjustment buckle 38 (see FIG. 5), so as to allow different degrees of tightening according to the contour of the leg segment and according to the needs of individual patients.

Figure 4:
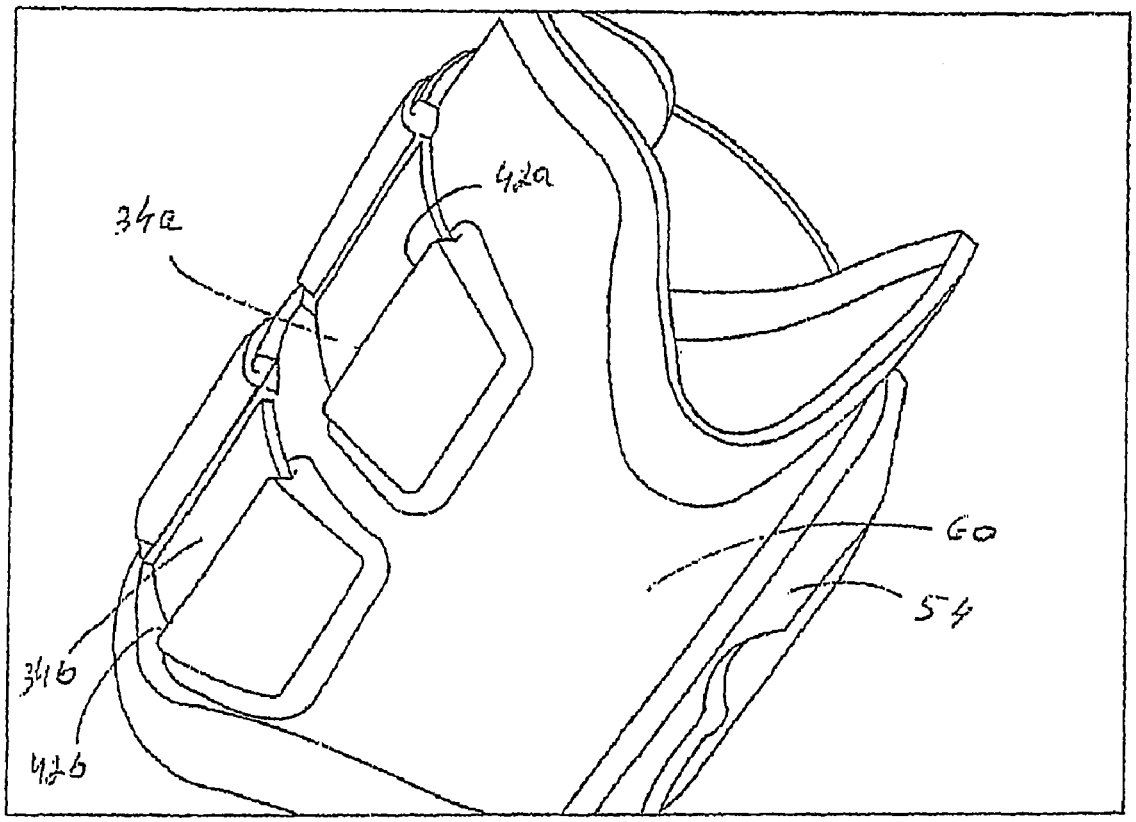
FIG. 4 is a perspective view showing a tightening mechanism of the inventive FES orthosis.

As previously mentioned, central frame 50 is covered by an external layer 60, which is made of a soft, preferably aesthetic material. Elastic straps 34a and 34b emerge through openings 42a and 42b in external layer 60, as shown in FIG. 4. This configuration eliminates or greatly reduces the distortion of central frame 50 during the securing of orthosis 150 to the leg.

Handle 54 is preferably made of an elastomeric material that imparts a flexible nature to handle 54. Preferably, handle 54 has a generally loop-like shape (hollow, with a rectangular or oval perimeter), so as to fit around stimulator cradle 30, or around any other connecting point or protuberance extending from frame 50, thereby securely locking orthosis 150 in place over the limb segment. Once positioned around stimulator cradle 30, handle 54 helps to protect stimulation unit 46 around the sides thereof, thereby providing stimulator cradle 30 and stimulation unit 46 with a smooth and unobtrusive profile. This is particularly important because knocks and pressures delivered to the surfaces of stimulation units of the prior art, in addition to being unpleasant for the user, can compromise the substantially even pressure applied by the surface electrode to the surface of the limb segment. The streamlined profile also facilitates rolling a pant leg past orthosis 150.

Fastening arrangement 34 is modular, can be easily detached from orthosis 150, and can be manufactured in several sizes.

Figure 5:
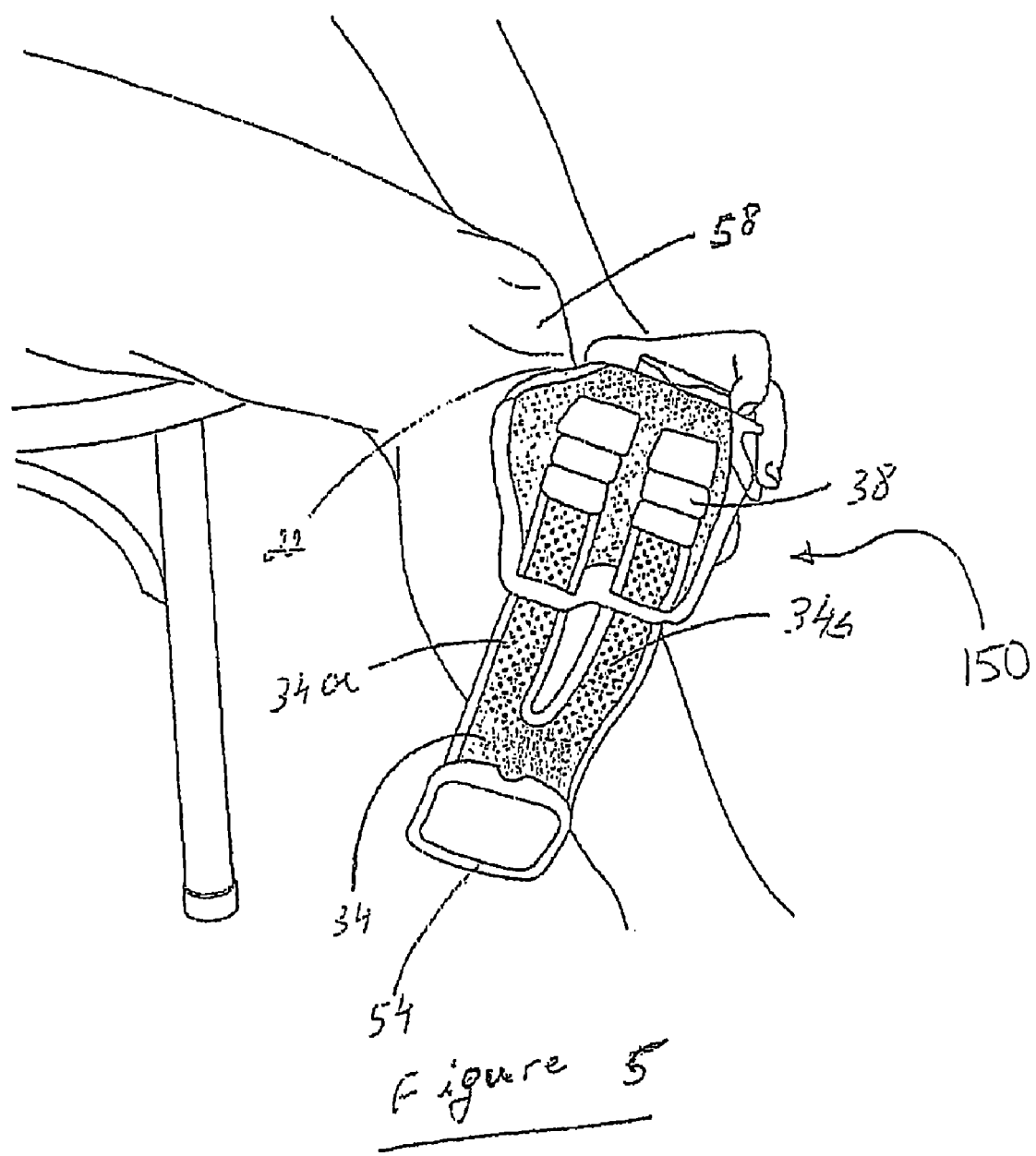
FIG. 5 illustrates a side view of the donning of the device of FIG. 1 on an impaired leg.
Figure 6:
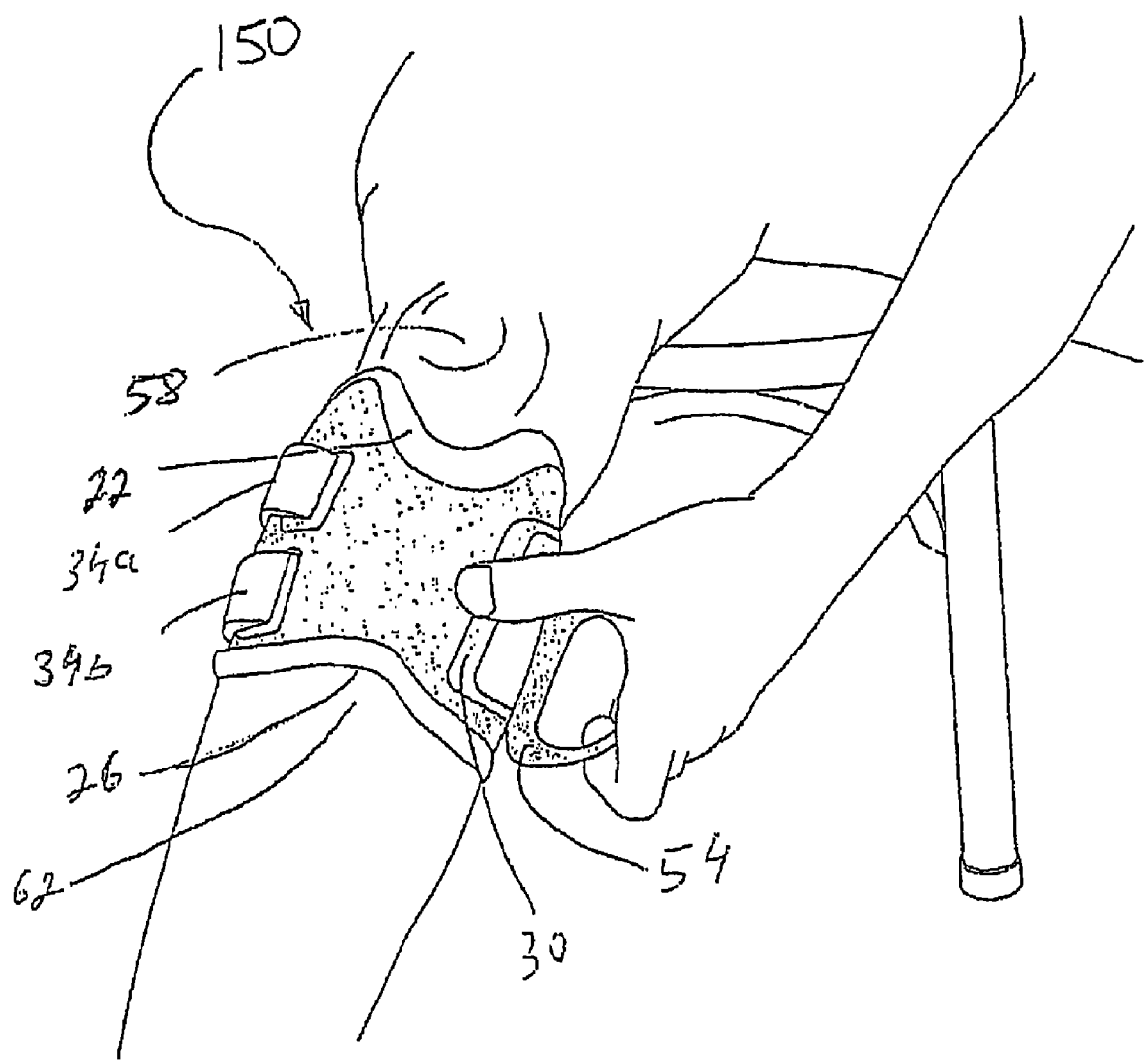
FIG. 6 illustrates a front view of the donning of the device of FIG. 1 on the impaired leg.

FIGS. 5 and 6 illustrate the donning—and subsequent locking—of FES orthosis 150 on an impaired leg. For positioning orthosis 150, while seated, it is preferable for the user to partially extend the lower leg, as shown in FIG. 5, such that the protuberance of the patella 58 is clearly defined. Subsequently, orthosis 150 is placed on the leg, such that upper locator 22 is juxtaposed against the lower facing of patella 58. Lower locator 26 should then be centered around tibial crest 62. Orthosis 150 grips the leg gently, but firmly enough to keep orthosis 150 in place, even if the user releases his grip as in the case, inter alia, of hemiplegic users. Subsequently, the securing of orthosis 150 is completed by means of fastening arrangement 34.

An alternative donning procedure is to place FES orthosis 150 along the tibial crest 62, a few centimeters below patella 58, and then to gently slide orthosis 150 up the calf until upper locator 22 abuts against patella 58. After orthosis 150 grips the leg segment so as to retain the desired position, locking is achieved by grasping handle 54 with the fingers of the opposite hand from the leg with orthosis 150. The thumb is placed on cradle 30, to hold orthosis 150 in place, and preventing sliding down or rotation, while the hand is closed so that the loop of handle 54 fits snugly around cradle 30. Alternatively, four fingers of the hand opposite to the leg with orthosis 150 are slipped through handle 54, grasping the handle close to cradle 30. The fingers then curl onto the attachment point of cradle 30 and lever handle 54 into place while allowing handle 54 to slip off the fingers. Once handle 54 is locked in place around cradle 30, the tension of fastening arrangement 34 firmly holds orthosis 150 around the limb segment of the user, even during aggressive movement of the limb.

FES orthosis 150 is doffed by releasing handle 54 from cradle 30 and pulling orthosis 150 away from the leg segment. It should be emphasized that both donning and doffing may easily be performed, unassisted and using a single hand, by hemiplegic patients.

Members 10a to 10d and member 14 of central frame 50 are preferably made of a polymeric material that provides flexibility and spring-like characteristics to orthosis 150. This combination of structure and materials provide the following features to orthosis 150:

1. Facile placement on the leg using a single hand.
2. Spring-loaded retention or gripping of orthosis 150 in proper position prior to and during locking orthosis 150 in position. Both the facile placement of the orthosis and the self-retaining grip of the orthosis on the leg enable patients suffering from an impaired hand to effectively don the device.
3. Accurate locating and relocating of the stimulating electrode assemblies.
4. After locking of orthosis 150 on the limb, the structure and materials of these members prevent random movement and migration of orthosis 150, even during limb extensions, flexions and gait.
5. Uniform dispersion of the pressure and strains to the limb tissue, thus retaining the natural profile and geometry of the limb tissue and muscle.
6. Uniform pressure of the electrodes against the surface of the limb segment.

Figure 7:
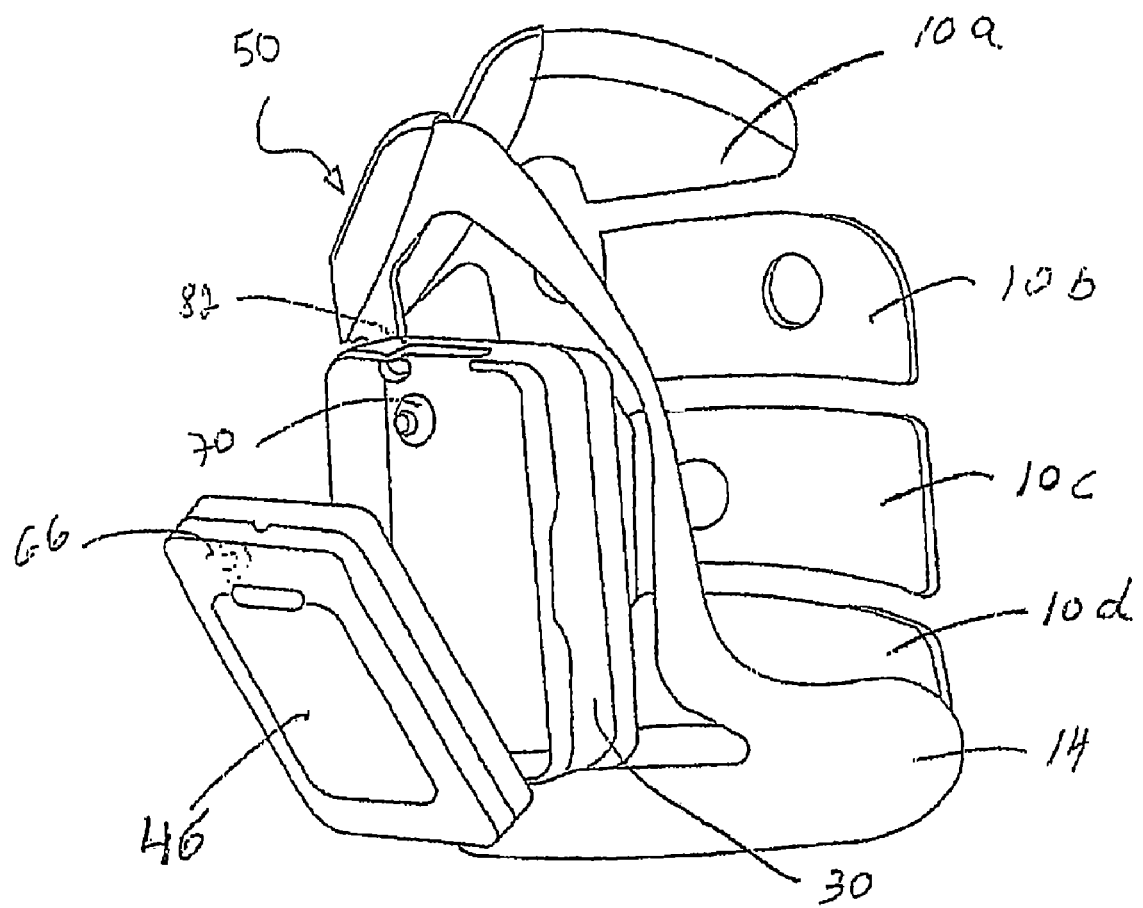
FIG. 7 is a perspective view showing the attachment of a neuroprosthetic stimulator unit to the FES orthosis of FIG. 1.

Referring now to FIGS. 1, 3 and 7, stimulator unit 46 is associated with orthosis 150 by means of cradle 30, which is a receptacle integrated onto the external surface of central frame 50.

Cradle 30 is advantageously designed to have concave edges for receiving a thumb during the donning procedure. Placing the thumb on the edges of cradle 30 enables the formation of a counter-force for urging handle 54 towards cradle 30. The backside of cradle 30 has a concavity similar to that of central frame 50, such that the overall contour can adapt to the contour of the limb segment.

Stimulator unit 46 is small and has a thin profile, so as to minimally protrude from the surface of orthosis 150, and is lightweight, to avoid superfluous weight on the impaired leg.

Figure 8:
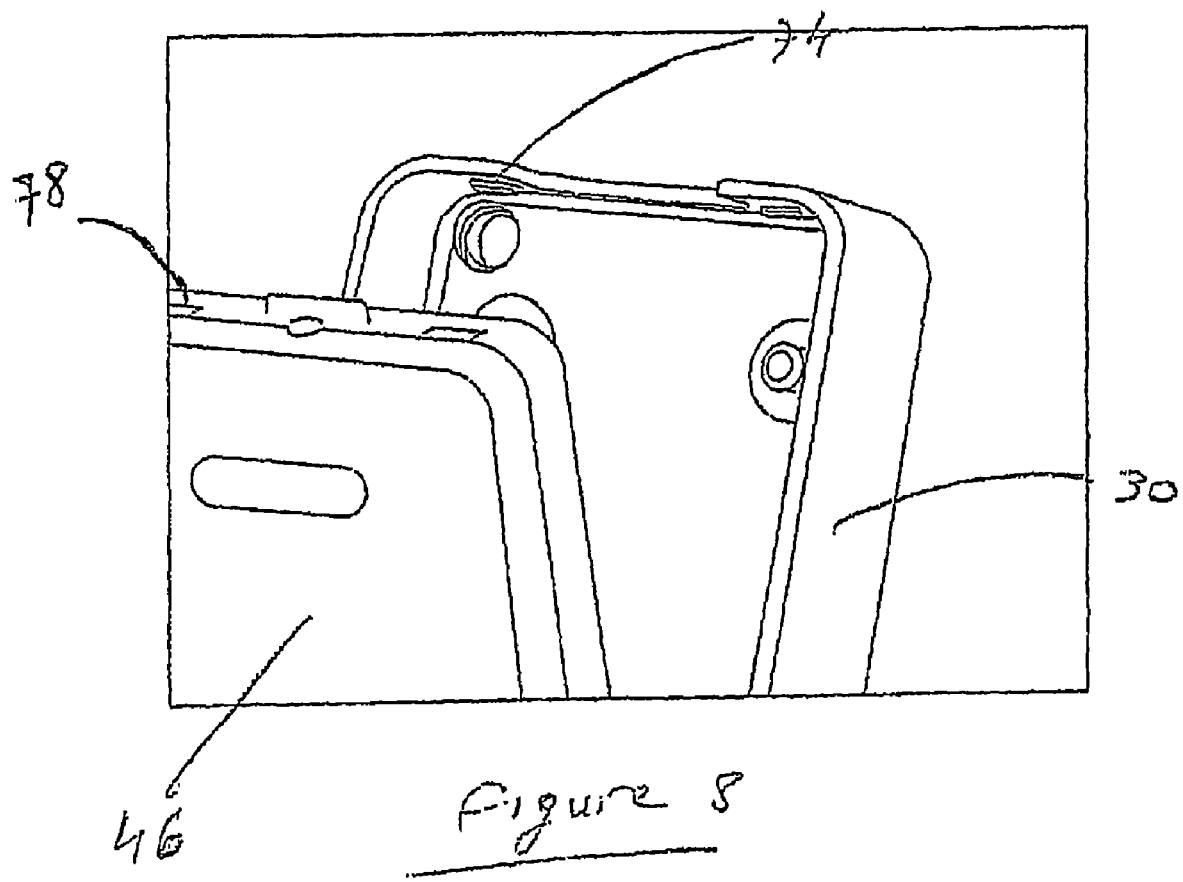
FIG. 8 illustrates the association of the neuroprosthetic stimulator unit with a cradle of the FES orthosis of FIG. 1.

Stimulator unit 46, as shown in FIGS. 7 and 8, is electrically connected to cradle 30 by connectors 66 and 70 disposed on stimulator unit 46 and on cradle 30, respectively. In one preferred embodiment, these connectors are complementary connectors. As shown, connector 66 is a complementary female snap, and connector 70 is a corresponding male snap. Stimulator unit 46 is mechanically connected to cradle 30 by complementary mechanical connectors 74 and 78. In the embodiment shown in FIG. 8, these connectors are female latch receiver 74 disposed on an edge of cradle 30, and female latch receiver 78 disposed on an edge of stimulator unit 46. An additional notch 82 in cradle 30 allows pulling stimulator unit 46 with a finger or thumb to release it from cradle 30. These connective features enable facile detaching and reattaching of stimulator unit 46 from, or to, cradle 30 using a single hand.

Figure 8A:
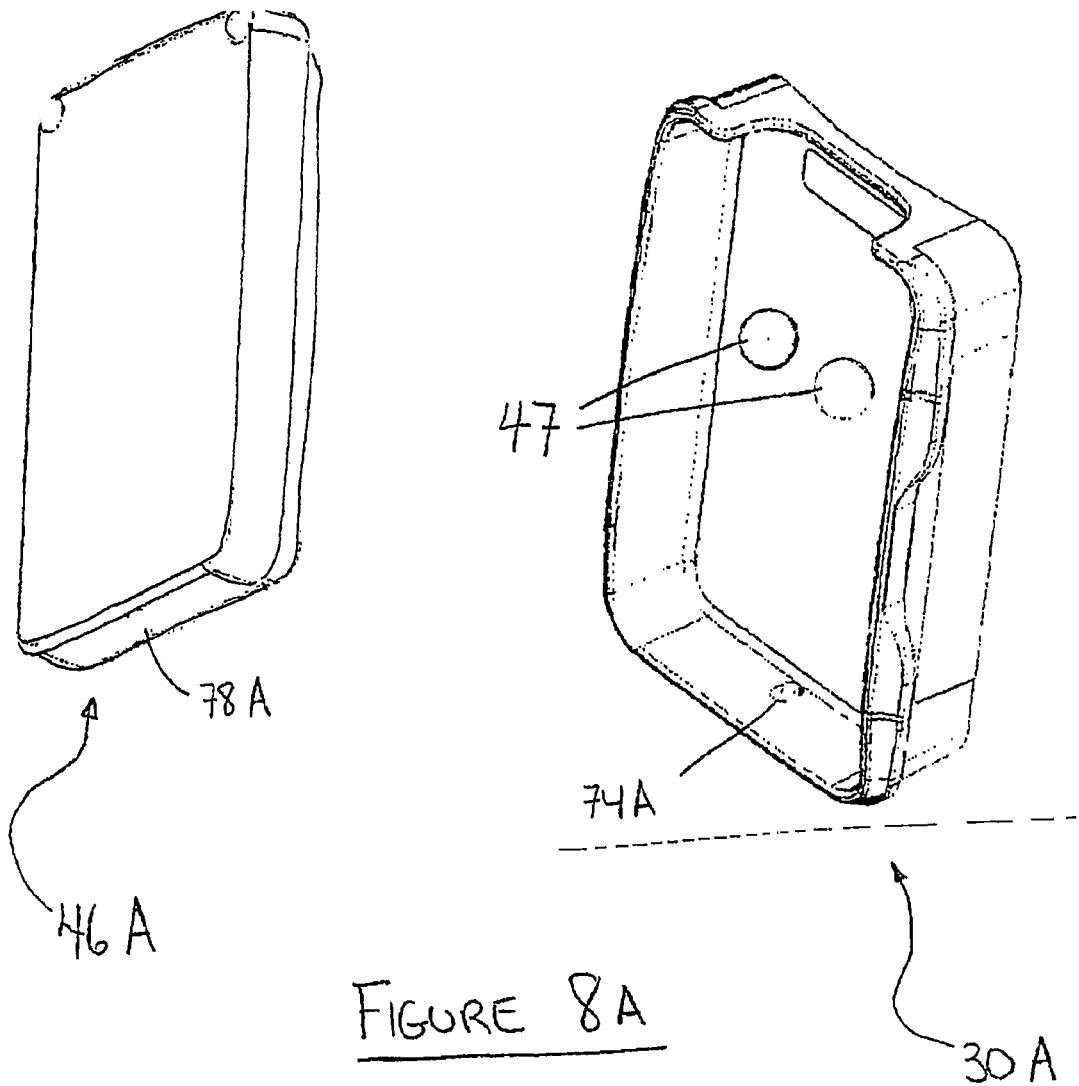
FIG. 8A is a perspective view showing a neuroprosthetic stimulator unit and a complementary receptacle or cradle for disposing on the FES orthosis, according to a preferred embodiment of the present invention.

FIG. 8A is a schematic perspective view showing a neuroprosthetic stimulator unit 46A and a complementary cradle 30A, according to a preferred embodiment of the present invention. As in the embodiments shown in FIGS. 7 and 8 and described hereinabove (with reference to stimulator unit 46 and cradle 30), stimulator unit 46A is electrically connected to cradle 30A by conducting connectors disposed on stimulator unit 46A and on cradle 30A, respectively (not shown). The electrical connection to the orthosis is via at least one opening 47 in the back panel of cradle 30A. Preferably, a complementary connector such as a snap connector is disposed in each opening 47 (see connectors 66 and 70 in FIG. 7 and the associated text hereinabove).

Stimulator unit 46A is mechanically connected to cradle 30A by complementary mechanical connectors 74A and 78A of the pin and recess variety. In FIG. 8A, stimulator unit 46A is equipped with a pin 78A disposed on a side facing, and cradle 30A is equipped with an opening 74A disposed in the respective side facing, such that upon inserting stimulator unit 46A into cradle 30A, pin 78A is introduced into opening 74A. Once stimulator unit 46A is snapped into cradle 30A, pin 78A is locked into place within opening 74A, thereby affixing stimulator unit 46A to the orthosis and ensuring a secure electrical connection between stimulator unit 46A and the electrodes, even when various mechanical strains are exerted on the orthosis during the course of physical activity.

Figure 9:
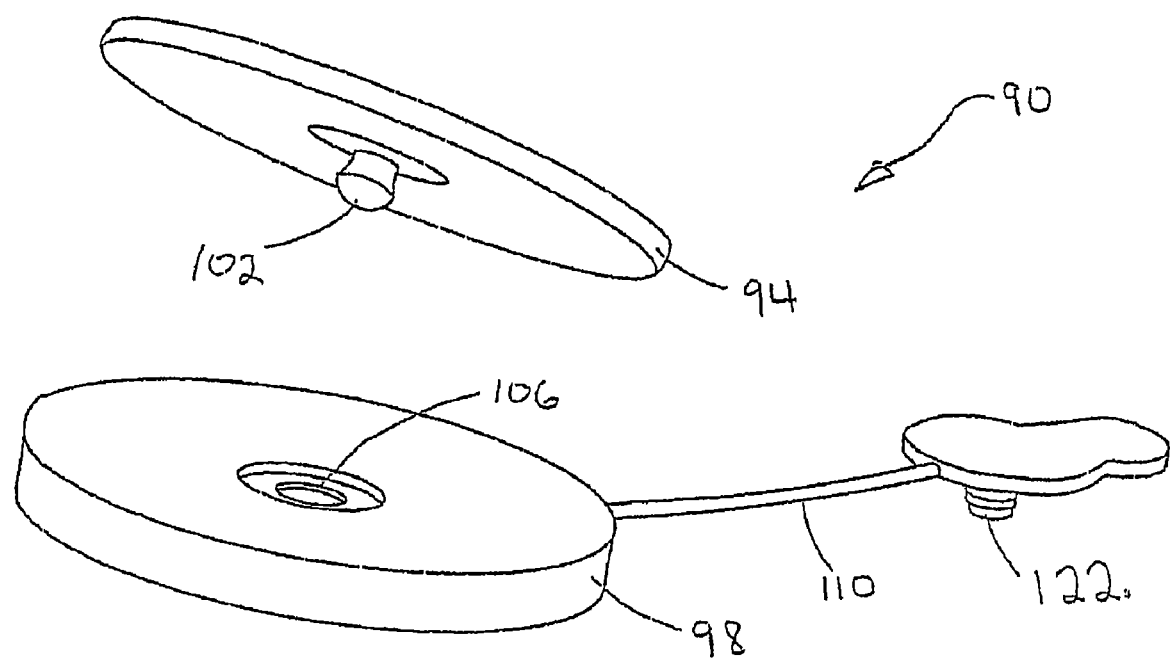
FIG. 9 is a perspective view of an electrode assembly of the inventive FES orthosis of FIG. 1.
Figure 9B:
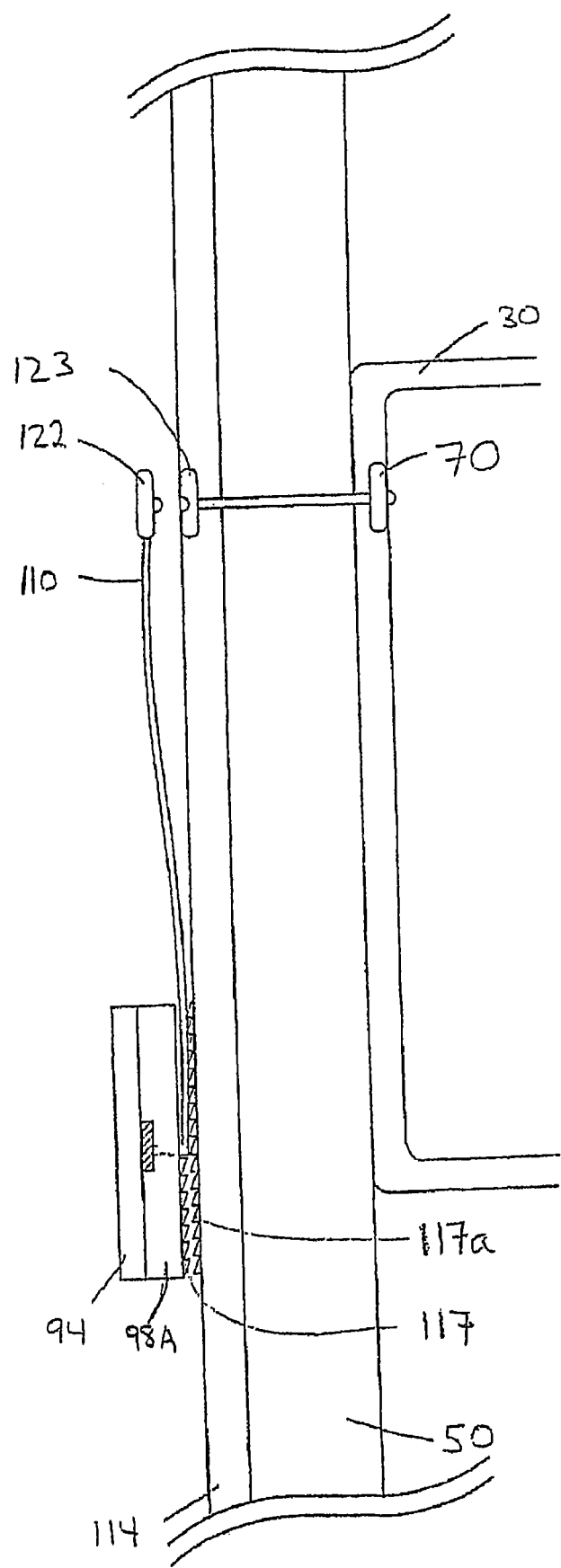
FIG. 9B is a schematic side view of a portion of the inventive FES orthosis, showing electrical and mechanical connections between the layers of the orthosis.
Figure 10:
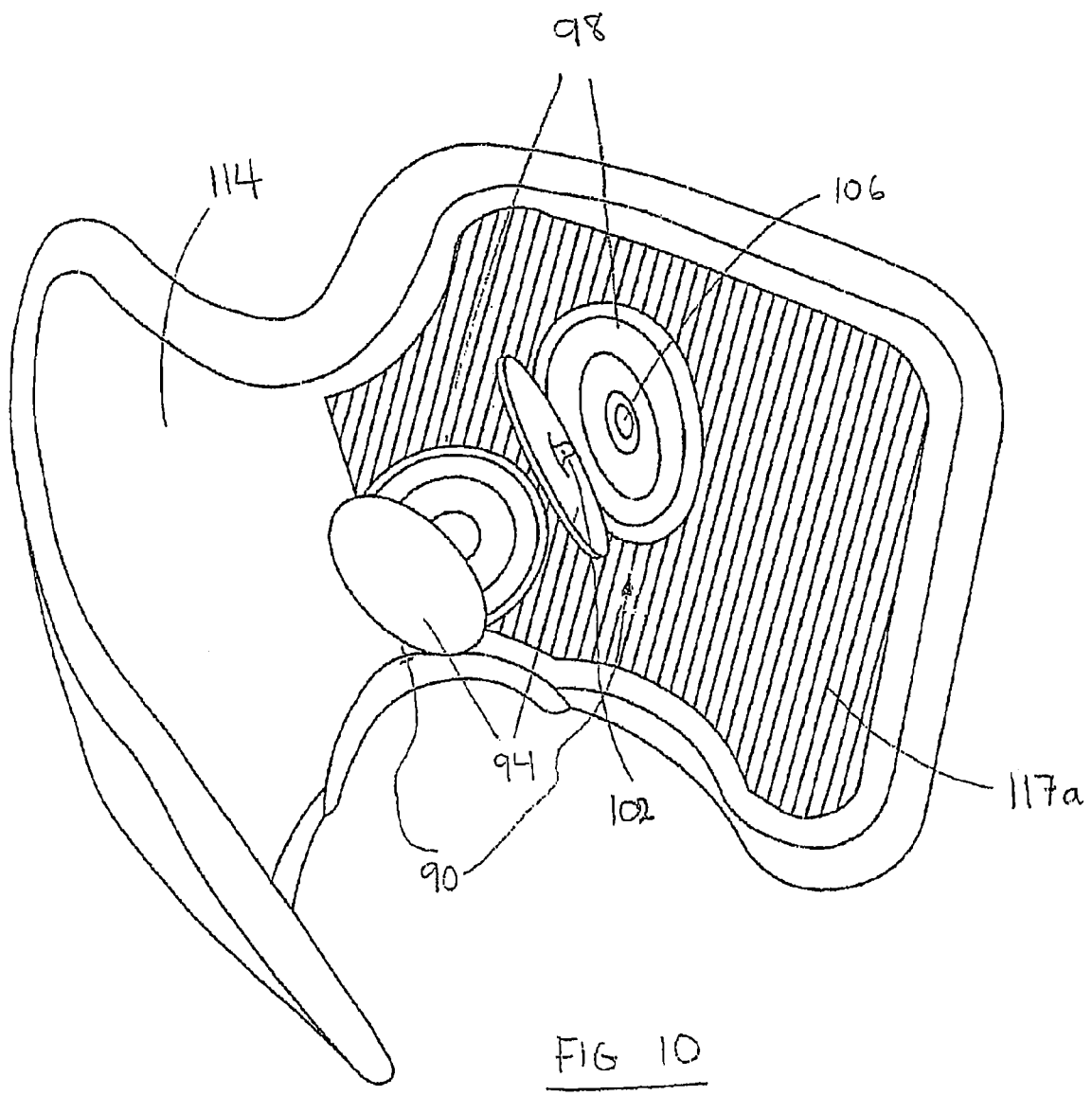
FIG. 10 is a perspective view of two electrode assemblies of FIG. 9 attached to an internal soft layer of the device of FIG. 1.

Referring now to FIG. 9, FIG. 9B and FIG. 10, FIG. 9 is a perspective view of an electrode assembly 90 of inventive orthosis 150 (not shown). Electrode assembly 90 includes a surface electrode 94, an electrode base 98, and complementary conductive connectors 102 and 106. Electrode assembly 90 further includes a conductive wire 110, which, at a first end, is mechanically connected to electrode base 98 so as to provide an electrical connection to connector 106. Conductive wire 110 terminates at a second end with a complementary conductive connector 122, which mechanically connects electrode assembly 90 to central frame 50 (as shown below in FIG. 9B), and electrically connects electrode assembly 90, via central frame 50, to stimulator housing 30 (also shown below in FIG. 9B).

In the exemplary embodiment shown in FIG. 9, complementary connector 102 is a male snap connector associated with surface electrode 94, while complementary connector 106 is a female snap connector connected to electrode base 98. Both surface electrode 94 and electrode base 98 are made of flexible materials that enable them to conform to the limb tissues.

Electrode base 98 is preferably concave-shaped, such that the connection between complementary connector 102 of surface electrode 94 and complementary connector 106 of electrode base 98 is recessed within a recess, thereby preventing excessive local pressure of the snaps 102 and 106 on the underlying skin. The concave, 3-dimensional shape of the top surface of electrode base 98 also provides a substantially even contact pressure of surface electrode 94 to the skin.

Surface electrode 94 preferably has a large surface area, with respect to many FES leg devices of the prior art, which serves to assuage discomfort from the electrical stimulation. The surface area of surface electrode 94 is preferably at least about 9 cm$^2$, more preferably at least about 12 cm$^2$, and even more preferably, at least about 15 cm$^2$. In some cases, the surface area of surface electrode 94 is as much as about 20 cm$^2$. It is presently preferred that the surface area of surface electrode 94 is within a range of 12-20 cm$^2$. By sharp contrast, the surface area of each surface electrode of the prior art devices such as the WalkAide® device is less than about 5-7 cm$^2$.

In contrast to prior art FES leg devices, the electrode separation in the FES orthosis of the present invention is preferably as large as anatomical constraints permit, particularly in the direction along the length of the limb. The distance between electrode centers is at least about 5 cm and the longitudinal separation is at least about 3 cm, and preferably at least 3.5 cm.

FIG. 9A is a perspective view of another embodiment of an electrode assembly 90A of inventive orthosis 150 (not shown). Electrode assembly 90A includes a surface electrode 94A, an electrode base 98A, and a wire 110, which terminates with complementary connector 122. In the exemplary embodiment shown in FIG. 9A, surface electrode 94A has first and second faces 95, 97 made of hydrogel or any another conductive, adhesive material known in the art for use in surface electrodes. First face 95 is for flexibly adhering to the skin of the user, while the opposite second face 97 is for adhering to a top face 99 of electrode base 98A. On top face 99 is disposed a conductive region 106A, for electrically connecting with second face 97. Preferably, top face 99 of electrode base 98A is also provided with a rim 101 for tightly receiving surface electrode 94A, such that the relative position of electrode 94A and electrode base 98A is uniquely defined and determined. The connection of electrode 94A and electrode base 98A may be further enhanced by disposing, on top face 99 of electrode base 98A, patches 103 of hook fasteners (e.g., plastic Velcro® hooks), which surprisingly hold on to the substantially flat, hydrogel surface of second face 97.

Substantially as described above with respect to FIG. 9, conductive wire 110 is mechanically connected to electrode base 98 so as to provide an electrical connection to conductive region 106A.

Figure 9D:
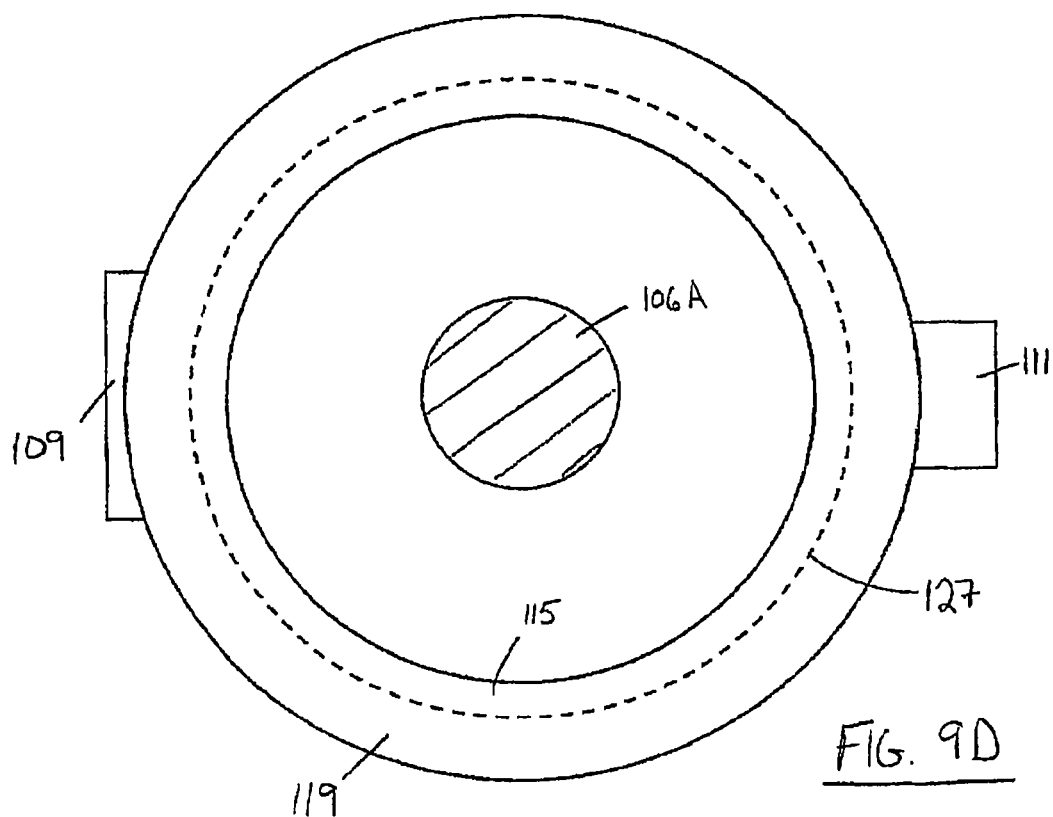
FIG. 9D is a schematic top view of the inventive electrode assembly of FIG. 9C.
Figure 9C:
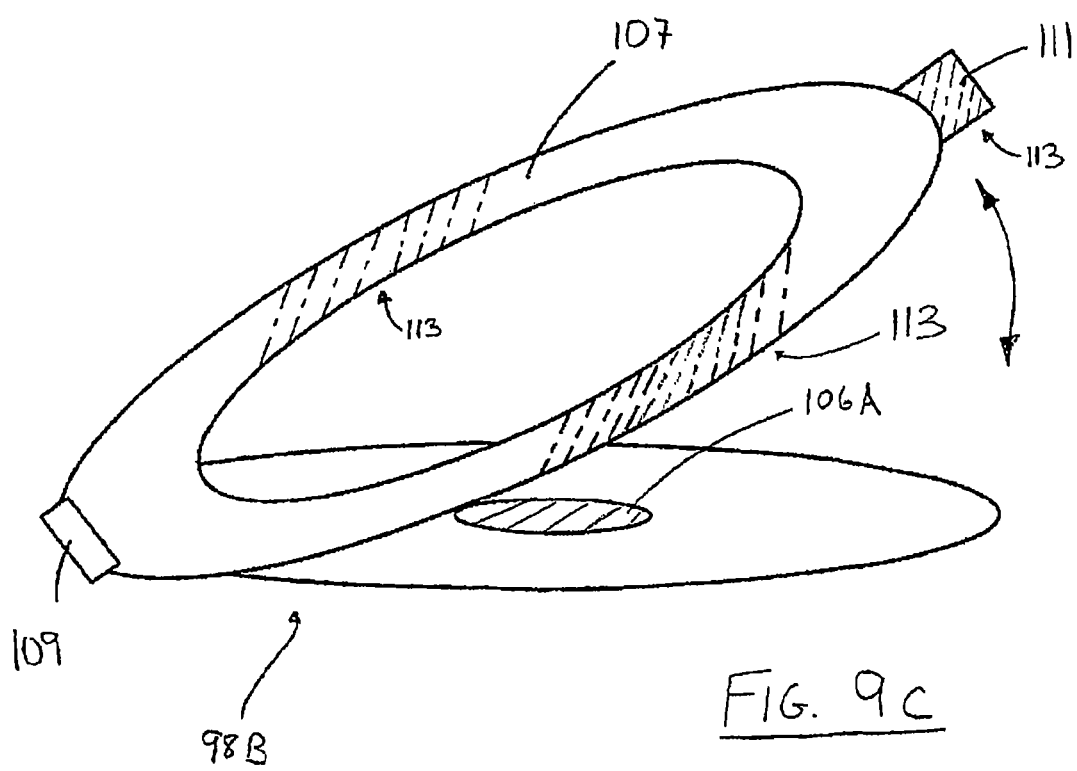
FIG. 9C is a schematic perspective view of an electrode assembly having an electrode base and a ring-shaped cover, according to another embodiment of the present invention.

Another preferred embodiment of an electrode base 98B according to the present invention is shown schematically in FIGS. 9C and 9D. As in previous embodiments, electrode base 98B is equipped with conductive region 106A, for electrically connecting with a face of a surface electrode such as surface electrode 94A (shown in FIG. 9A). Electrode base 98B is also equipped with a cover such as ring-shaped cover 107. Cover 107 is preferably connected to electrode base 98B by means of a hinge 109, which in one preferred embodiment, is obtained simply by attaching (e.g., by ultrasonic welding) cover 107 to electrode base 98B. Alternatively, base 98B and cover 107 can be manufactured as one piece, which is subsequently folded in the middle to create hinge 109.

After insertion of the surface electrode between electrode base 98B and cover 107, cover 107 is pressed down in the direction of base 98B. A tongue 111 disposed roughly opposite hinge 109 facilitates opening and closing of cover 107.

Preferably, a bottom surface of cover 107 and tongue 111 is at least partially covered with complementary connectors 113, preferably hook and loop fasteners, for connecting to complementary connectors 117a on internal layer 114, shown in FIG. 9B and FIG. 10. Alternatively, complementary connectors 113 may be connected to complementary connectors 141 on a top facing 139 of a detachable layer 118 shown below in FIGS. 12A-12B.

Figure 14:
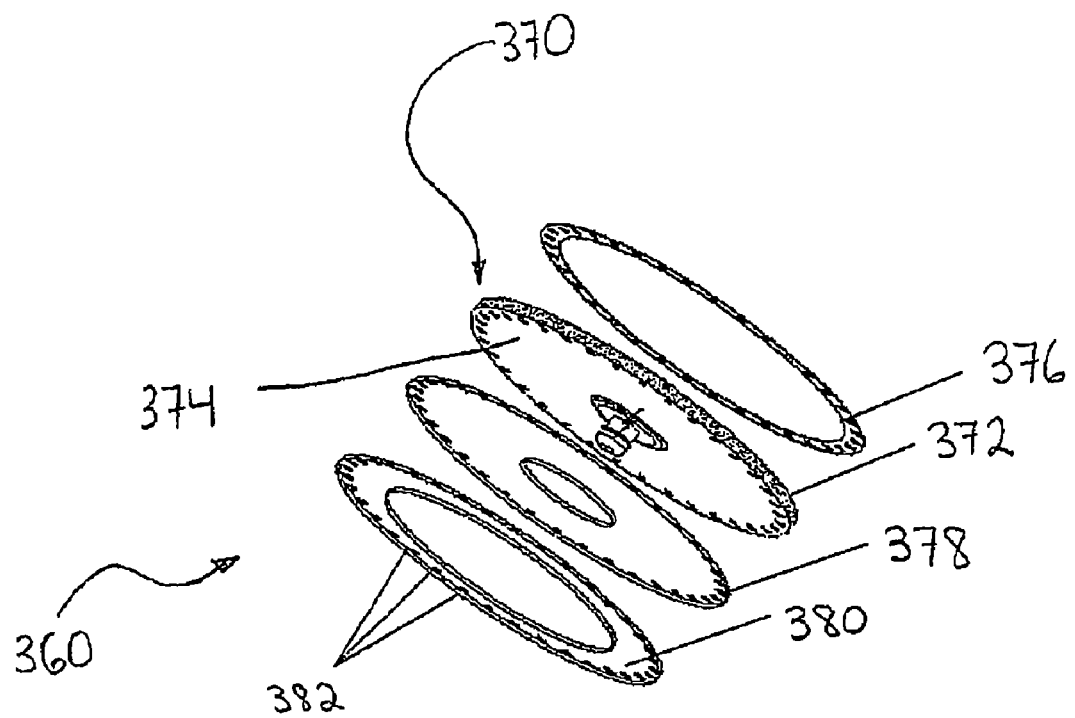
FIG. 14 is a schematic exploded view of the electrode according to another aspect of the present invention.

Cover 107 is adapted such that the perimeter of the surface electrode is held firmly in place. Also, cover 107 protects the edges of the hydrogel layer (see, by way of example, hydrogel layer 372 in FIG. 14 hereinbelow) to prevent or greatly reduce disintegration of the edges of the hydrogel layer.

A top view of cover 107 and electrode base 98B is provided in FIG. 9D. A dotted line 127 represents the circumference of electrode base 98B.

Electrode base 98B may advantageously have an edge or perimeter of a different color or texture than the rest of base 98B, so as to direct the user in affixing the surface electrode in the proper position on base 98B.

The electrode may also be attached directly to the orthosis, e.g., by attaching hook and loop fasteners to the face of the electrode facing the orthosis.

The relationship between electrode assembly 90 and internal soft layer 114, shown in FIG. 10, is also relevant for the alternative embodiment presented in FIG. 9A and described hereinabove. Electrode base 98 is attached to internal layer 114 by complementary connectors 117 and 117a, preferably hook and loop fasteners such as Velcro®, which are best seen in FIG. 9B.

The electrical connections are made as follows: complementary connector 122 connects to a complementary connector 123, which is disposed in a fixed position on internal layer 114 or on central frame 50. Electrical stimulation is achieved by directing a current from stimulator unit 46 (not shown), via connector 70 disposed on housing 30, through frame 50 and internal layer 114, to connector 123, and ultimately, to electrode assembly 90A and stimulator housing 30 with connector 123.

In the exemplary embodiments shown, complementary connector 122 is a conductive male snap connector, and complementary connector 123 is a conductive female snap connector.

It will be appreciated that the design of electrode base 98 and the design of connectors 122 and 123 enable a wide range of positioning of each electrode assembly 90. Unlike various prior art devices, the position of electrode 94 is not limited to a position in which electrode 94 physically touches a conductive element fixed in the body of the orthosis (such as connector 123). Rather, the position of electrode 94 is substantially decoupled with respect to such fixed conductive elements. Wire 110 should be long enough to enable the fall range of positioning.

In addition, the above-described design enables the clinician to exactly define the position of each electrode assembly 90 in a first step, and then, in a second step, to attach the assembly to FES orthosis 150 by means of complementary connectors 122 and 123. Thus, during the initial setup procedure, the clinician needs to position solely the surface electrodes or electrode assemblies (e.g., electrode assembly 90A)—and not the entire orthosis 150—on the stimulation points of the muscles to be activated. In order to define the exact position, the clinician activates the electrodes, which can electrically be connected directly to stimulator unit 46. Subsequently, the clinician connects each surface electrode 94 to the respective electrode base 98 prior to donning orthosis 150 on the leg and prior to attaching each electrode base 98 to internal layer 114 or to central frame 50. Once orthosis 150 has been donned, each electrode base 98 attaches, by means of complementary connectors 117 and 117*a* (shown in FIG. 9B), to internal layer 114 of orthosis 150.

Stimulation by means of the two electrode assemblies 90, illustrated in FIG. 10, produces dorsi-flexion of the foot. To ensure electrical contact between surface electrode 94 and the skin surface, surface electrode 94 may be smeared by conductive gel or hydrogel or covered by a cloth pad that has been soaked in a conductive liquid such as water. The face of surface electrode 94 for contacting the skin may advantageously be a flexible hydrogel layer.

Electrode assemblies 90 conform to the three-dimensional shape of the underlying limb, and adapt their shape during limb articulations and muscle contractions. Electrode base 98 and surface electrode 94, which are essentially elastic, lie pressed between internal soft layer 114 and the skin surface, such that a minimal resistance is supplied to the changing limb geometry.

Figure 11:
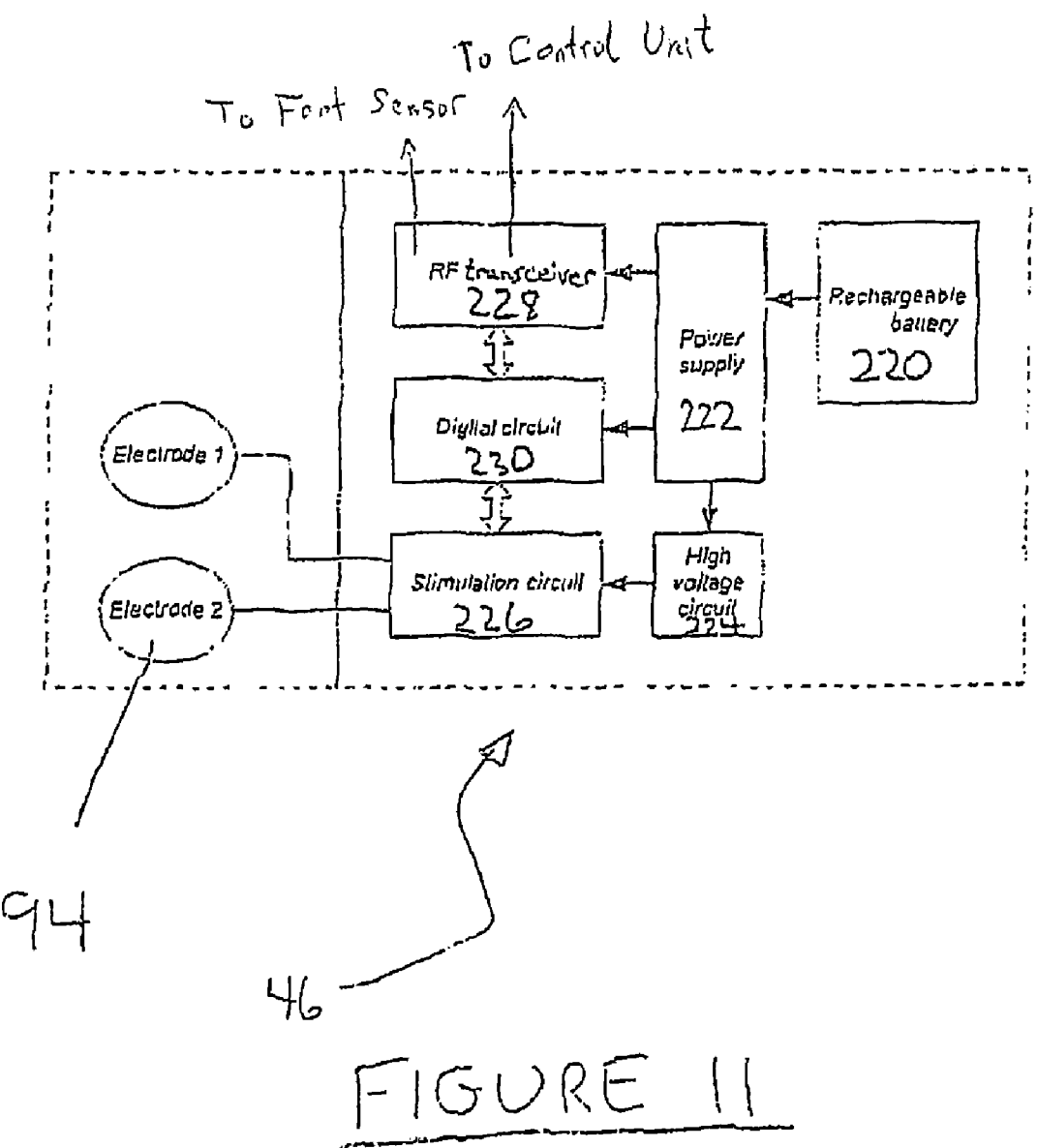
FIG. 11 is a block diagram showing the main features of the electrical stimulation unit.

Referring now to FIG. 11, stimulator unit 46 is electrically connected with at least one stimulation electrode, such as surface electrode 94. Stimulator unit 46 is preferably powered by a rechargeable battery 220 that is electrically connected to an internal power supply 222. Power supply 222 supplies power to a high-voltage circuit 224 feeding into stimulation circuit 226. Preferably, stimulator unit 46 communicates with a stimulator control unit and/or a limb or motion sensor (described hereinbelow) by means of a radio frequency (RF) transceiver 228. In a presently-preferred embodiment, RF transceiver 228 transmits signals to a control unit under normal circumstances. However, RF transceiver 228 transmits signals directly to the foot sensor device (described hereinbelow), under special, pre-defined circumstances, such as:

1. In the RF registration process (when the present sensor and/or stimulation unit are replaced by new ones, and are registered to each other and to the control unit), and
2. When there is a long period of sensor inactivity, the sensor requests the authorization from the stimulation unit to enter a sleep mode. The stimulation unit then transmits a signal to the sensor, indicating authorization granted or authorization denied.

Power supply 222 supplies power at a lower voltage to RF transceiver 228, and to a digital circuit 230 interfacing between RF transceiver 228 and stimulation circuit 226.

As used herein in the specification and in the claims section that follows, the term "radio frequency" refers to electromagnetic waves, preferably having a frequency within the radio frequency range. The currently preferred range is 2400-2483.5 GHz.

During operation, the battery-operated control unit maintains two-way communication with stimulator unit 46.

The control unit enables to switch on the device, select the operating mode of the device (gait mode, training mode, or returning to standby mode), and adjust the intensity of stimulation and volume of an audio alert.

Additionally, each of the system components (FES orthosis 150, control unit and foot sensor) is preferably represented by graphic icons on the control unit. LEDs of different colors emit light under the relevant icon so as to indicate attention-requiring events such as low battery or a malfunction of any individual component. Other LEDs indicate stimulating or resting, stimulation intensity, or training mode.

The control unit preferably has an audio alert that produces an audio signal so as to alert the user when: the system is first switched on, a button has been pressed, a mode has been selected, the battery is low, radio communication between components of the device is lost, or, other faults requiring the attention of the user have occurred. The control unit may be waist-mounted, hung by means of a neck strap, or mounted by an in-pocket hold.

The foot sensor unit may be any of various foot sensor units known in the art, including a force sensor disposed underneath the foot of a user, a tilt sensor, etc.

Figure 12A:
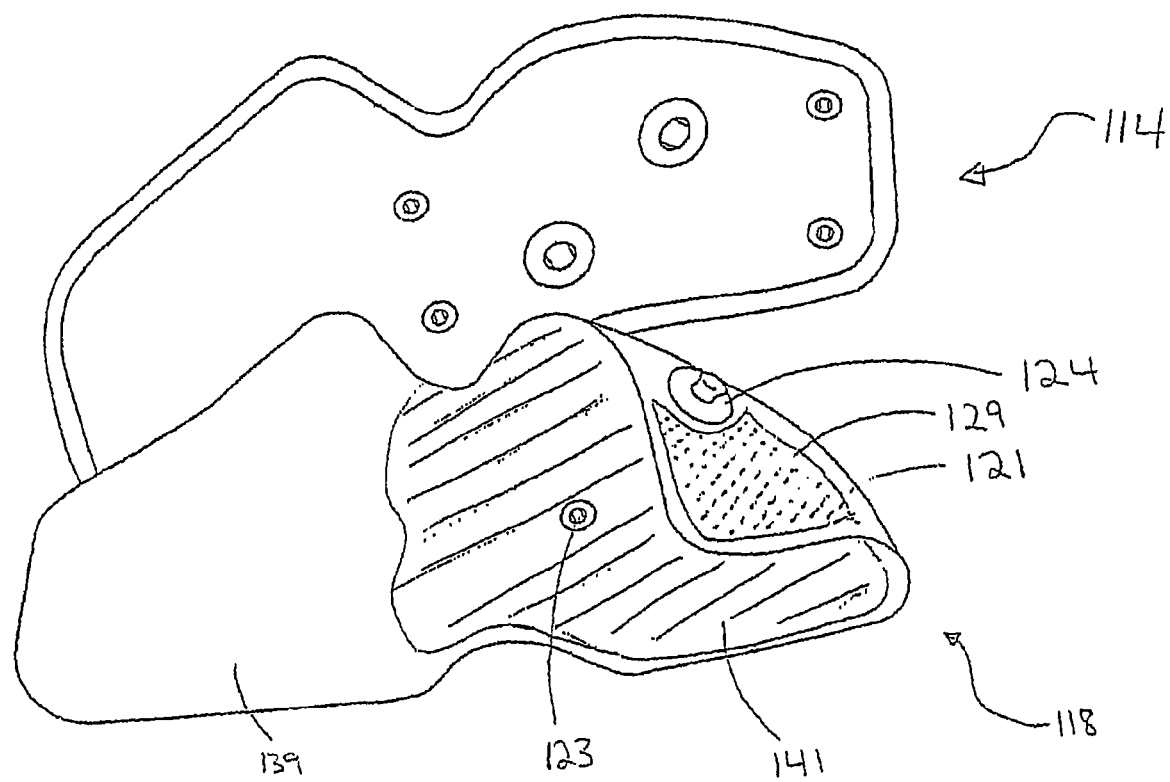
FIG. 12A is a front view of a detachable layer of the FES orthosis, according to one aspect of the present invention.
Figure 12R:
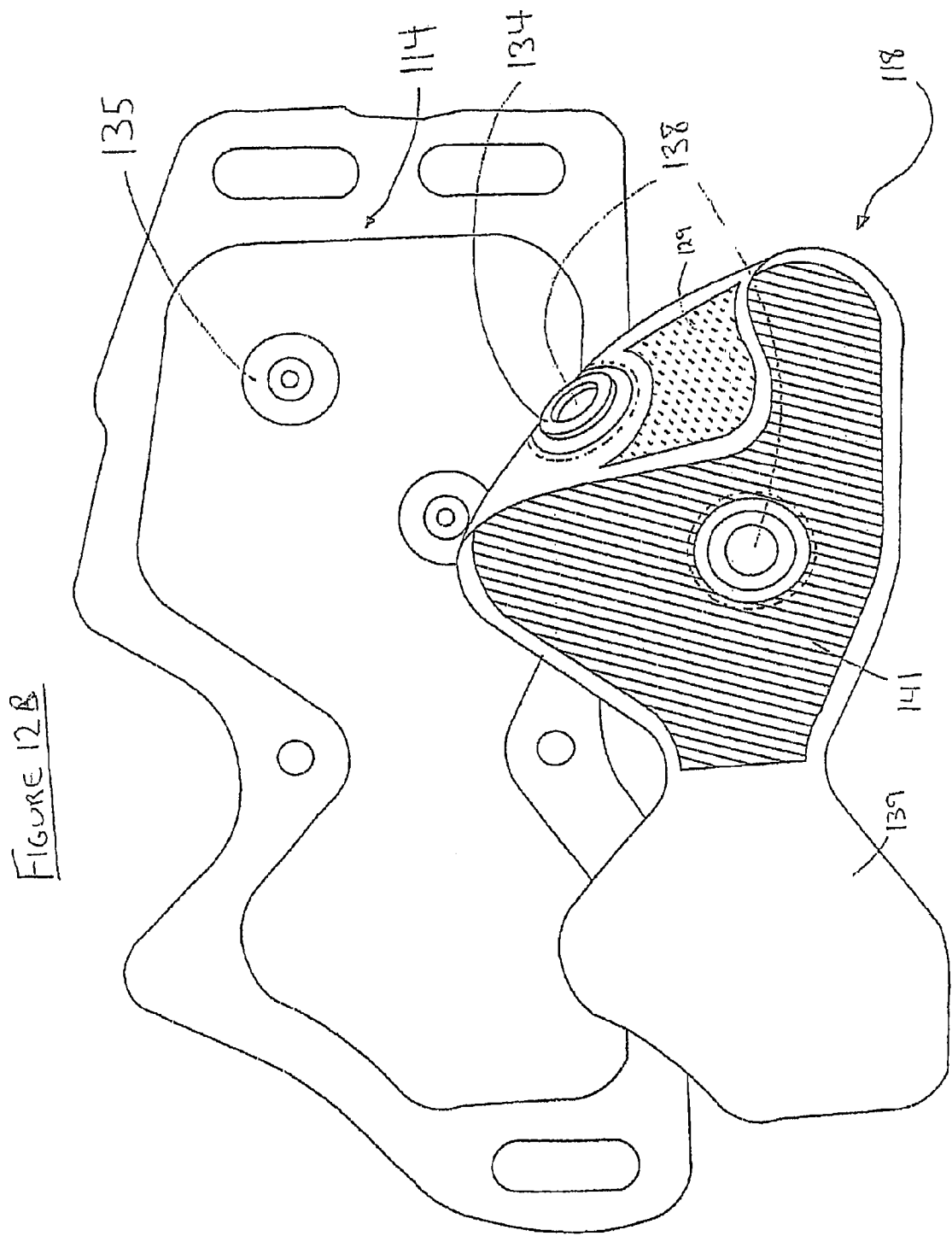
FIG. 12B illustrates another embodiment of the inventive detachable layer, having hollow snap connectors for securing the detachable layer to the internal layer of the orthosis.
FIG. 12C illustrates another embodiment of the inventive detachable layer, in which the layer covers only a portion of the surface of the internal layer of the orthosis.
FIG. 12D is a schematic cross-sectional side view of a slice of a portion of the inventive FES orthosis, showing some of the electrical and mechanical connections between the detachable lining and other components of the orthosis.
FIG. 12E is a schematic cross-sectional side view of a slice of a portion of the inventive FES orthosis, showing some of the electrical and mechanical connections between the detachable lining and other components of the orthosis, wherein the detachable lining is directly attached to the orthosis frame.
FIG. 12F illustrates another embodiment of the inventive detachable layer, in which the layer is stiffened by at least one supporting region.

FIGS. 12A-12F schematically depict another aspect of the present invention. FIGS. 12A and 12B show a front view of a personal panel or detachable layer or liner 118 for attaching to the orthosis, either to internal soft layer 114, as shown in a schematic side cross-sectional view of a slice of the orthosis in FIG. 12D, or directly to frame 50, as shown in the identical view in FIG. 12E.

Detachable layer 118 preferably has, substantially, the shape of internal soft layer 114. Detachable layer 118 is soft, so as to provide a comfortable feel on the skin surface of the user, but is provided with sufficient rigidity to maintain the alignment of each electrode assembly 90 and to make it easier to position detachable layer 118 to the orthosis. Suitable materials for detachable layer 118 include various non-woven materials such as Nordenia™ or Namliong™ loop. Detachable layer 118 preferably has a first or top facing 139 having a plurality of complementary connectors 141, such as loop fasteners, disposed on the surface.

Detachable layer 118 may include the compatible electrical connectors of internal layer 114. Thus, detachable layer 118 may include male snap connectors 124 on a second or back surface 121 facing FES orthosis 150 and complementary connectors such as female snap connector 123 on top facing 139, for receiving complementary connector 122 (shown in FIGS. 9, 9A, and 9B) and described hereinabove. In this arrangement, detachable layer 118 is attached by the clinician to internal layer 114, or to another portion of the orthosis, such as frame 50, by means of snap connectors 124. This provides the requisite electrical contact, and ensures accurate, singular, repeatable positioning and fixing of detachable layer 118 onto internal layer 114 and/or with respect to frame 50. Alternatively, back surface 121 has at least one patch 129 of hook or loop connectors that fix detachable layer 118 to internal layer 114. In FIG. 12A, by way of example, patch 129 includes hook connectors.

In another preferred embodiment, shown in FIG. 12B, detachable layer 118 includes holes 138, which are advantageously disposed to line up between complementary male connectors 122 of electrode assembly 90 and complementary female connectors 123 on internal layer 114, such that connector 122 connects electrode assembly 90—mechanically and electrically, to stimulator unit housing 30.

It must be emphasized that the repositioning of detachable layer 118 on FES orthosis 150, for a particular individual, restores accurate, substantially repeatable positioning of the electrode assemblies 90, even when FES orthosis 150 is a standard, universal unit that has not been adapted to the needs of that individual. Thus, in sharp contrast to prior art devices, inventive detachable layer 118 enables the clinician to use a single FES orthosis 150 for treating many users in the clinic. An individual detachable layer 118 is dedicated for a particular user. Each particular user undergoes a pre-fitting session with the clinician, so as to customize the electrode positioning for the needs of that user. Subsequently, detachable layer 118 is used repeatedly in future clinical sessions of the user. The clinician, who works with many users each day, simply removes the pre-fitted internal soft layer belonging to the previous user and attaches the pre-fitted internal soft layer belonging to the current user. The detachable layer also serves as a hygienic layer where the device is shared between users.

The replacement of the detachable layer 118, with no need to relocate the electrode assemblies 90 for each patient, enables the clinician to provide efficient, effective treatment to numerous orthosis users in a short period of time. Detachable layer 118 is preferably disposable. Alternatively, detachable layer 118 is washable.

According to another preferred embodiment of the present invention, shown schematically in FIG. 12B, a hollow snap connector 134, which is preferably an annular or oval hollow snap connector, is associated with a perimeter of hole 138 of detachable layer 118. Hollow snap connector 134 accurately and reliably snaps into a corresponding hole or recess 135, thus ensuring that detachable layer 118 is tightly attached to internal layer 114, and is exactly positioned in the same location upon each application. In addition, hollow snap connector 134 also serves for mechanically attaching complementary connector 122 of electrode assembly 90 to internal layer 114, via detachable layer 118.

Hollow snap connector 134 can be made of a plastic, flexible material such as PVC.

Figure 12C:
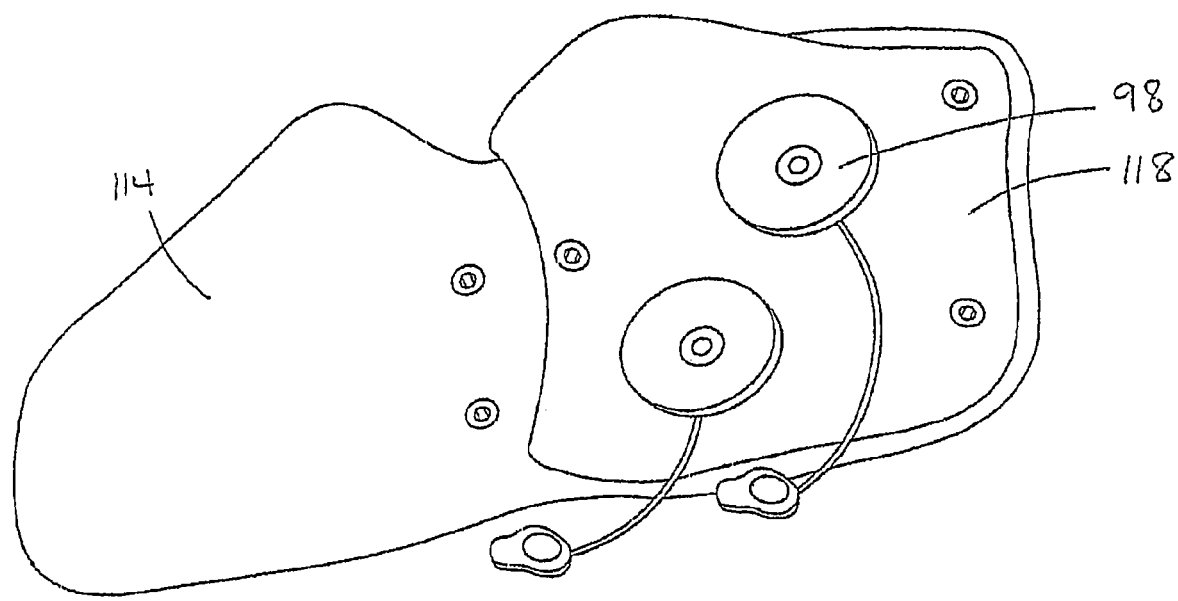

It should be appreciated that detachable layer or liner 118 may also have a shape other than the contour of internal layer 114. For example, detachable layer 118 may cover only a portion of the surface of orthosis 150, as shown in FIG. 12C. FIG. 12C also shows electrode base 98 affixed to detachable layer 118.

Figure 12E:
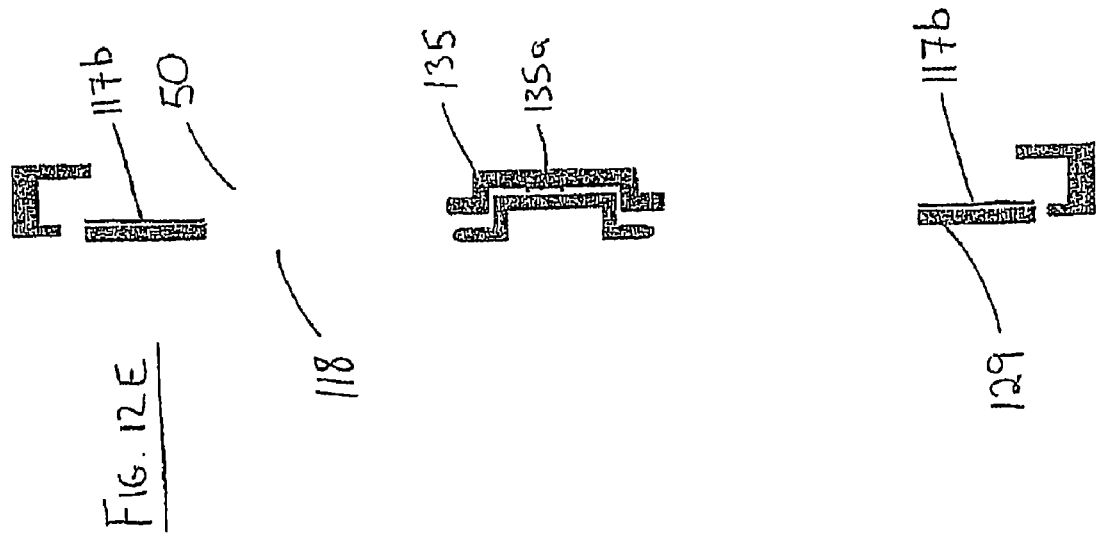
Figure 12D:
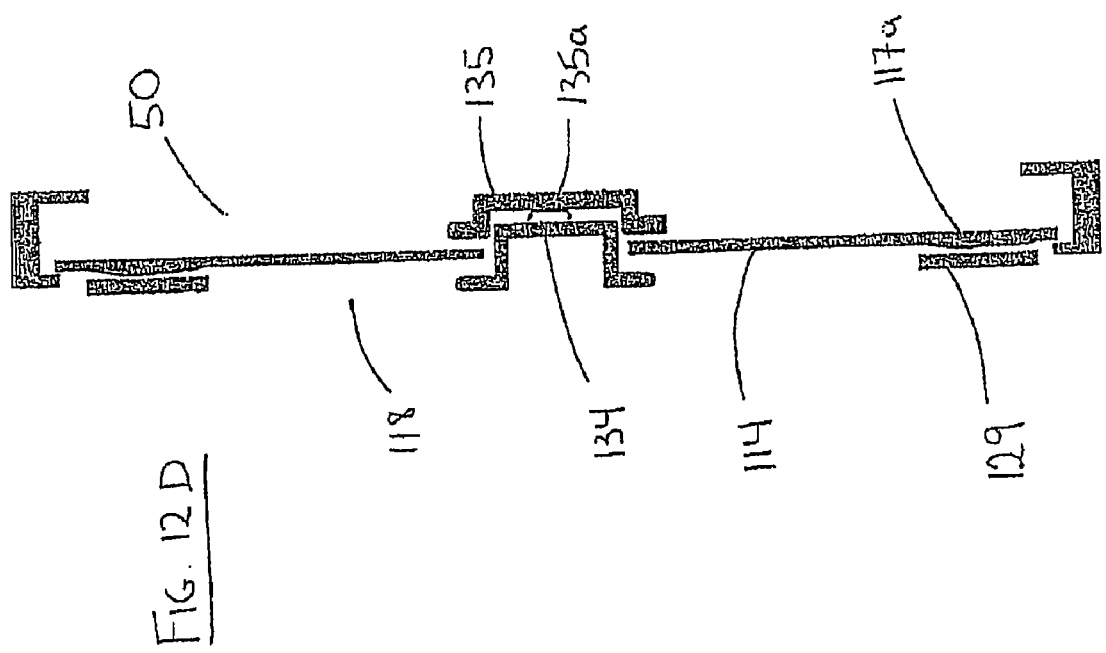

FIGS. 12D and 12E, described briefly hereinabove, show some of the main electrical and mechanical connections between detachable layer 118 and other components of the orthosis, wherein, in FIG. 12D, detachable layer 118 is attached to central frame 50 and to internal layer 114, and wherein, in FIG. 12E, layer 118 is directly attached to central frame 50.

In FIG. 12E, a complementary connector such as hollow snap connector 134, is disposed on detachable layer 118. Hollow snap connector 134 accurately and reliably snaps into a corresponding hole or recess 135 disposed in central frame 50, so as to directly connect detachable layer 118 to central frame 50. This also ensures that detachable layer 118 is tightly associated with internal layer 114, and that detachable layer 118 is exactly positioned, with respect to central frame 50, in the same location upon each application.

As described hereinabove with reference to FIG. 12A, back surface 121 of detachable layer 118 preferably has at least one area or patch 129 of complementary connectors (e.g., hook or loop connectors) that fix detachable layer 118 to internal layer 114 (via complementary connectors 117a).

The description of the attachments of FIG. 12D largely applies to those of FIG. 12E. In FIG. 12E, however, detachable layer 118 is juxtaposed against central frame 50, consequently, patch 129 of complementary connectors on back surface 121 is configured to fix detachable layer 118 to central frame 50 by means of complementary connectors 117b.

In another preferred embodiment, inventive detachable layer 118 is stiffened by a supporting region or frame. A first side of detachable layer 118 is schematically provided in FIG. 12F. Detachable layer 118 is largely similar or even substantially identical to detachable layer 118 described hereinabove, and can be connected to an internal layer of the orthosis, or to another portion of the orthosis, in similar or identical fashion. Preferably, the first side of detachable layer 118 has a plurality of complementary connectors 141A, preferably, hook or loop fasteners, disposed thereon. Typically, complementary connectors 141A are disposed within distinct fields or regions 142A on detachable layer 118.

At least one supporting region 143 of a stiffening or supporting material are attached to detachable layer 118, in order to temper the flexibility of detachable layer 118. The disposition of supporting region 143 on detachable layer 118 simplifies the assembly process of detachable layer 118 on the orthosis and also ensures that detachable layer 118 has a smooth, unwrinkled surface. Polypropylene is one suitable material for region 143. The attachment of region 143 to underlying detachable layer 118 may be performed by sewing, gluing, or other means known to those skilled in the art.

Figure 12F:
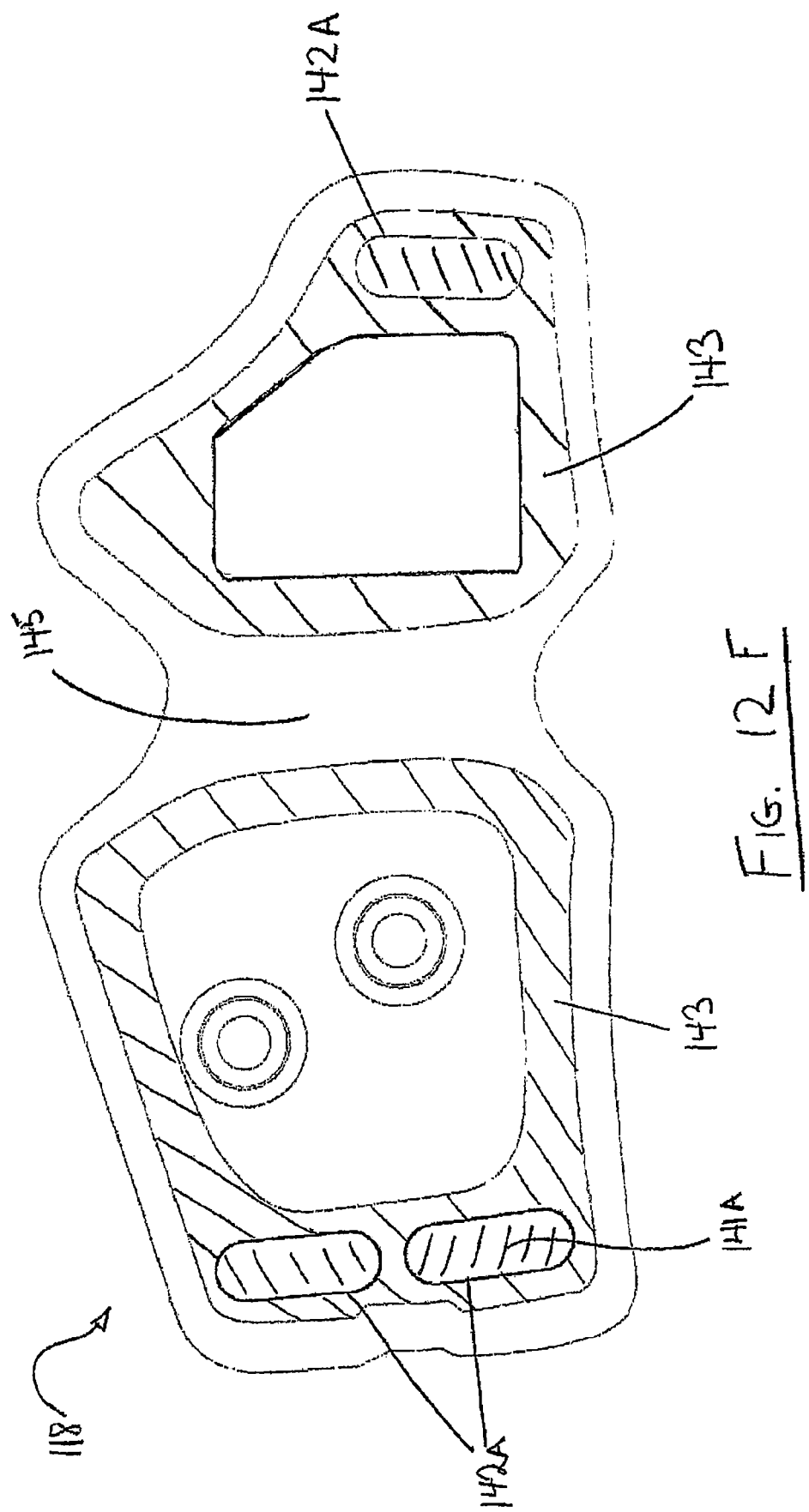

As shown in FIG. 12F, an area 145 on detachable layer 118 is preferably free of supporting material, so as to enable detachable layer 118 to flexibly bend around the leg of the user without undue mechanical stress, and to allow at least part of detachable layer 118 to "breathe", thereby avoiding excessive perspiration.

With reference to FIGS. 13A-C, and FIGS. 12D-E, FIG. 13A is a schematic perspective view of electrode assembly 90 and detachable layer 118, according to another embodiment of the present invention. As above, detachable layer 118 is equipped with hollow snap connector 134, which, as shown and described hereinabove, is configured to accurately and reliably snap into a corresponding complementary recess 135 disposed in central frame 50, so as to directly connect detachable layer 118 to central frame 50.

A complementary conductive connector 222 of electrode assembly 90 has a conductive snap 222B (shown in FIG. 13C) designed to pass through a hole such as hole 138 of hollow snap connector 134, and into a complementary area 135a of complementary recess 135 so as to both mechanically and electrically connect electrode assembly 90 to central frame 50. The perimeter of complementary conductive connector 222 has fins or protruding elements 222A, for snap connecting into the complementary contour of hollow snap connector 134.

Thus, hollow snap connector 134 mechanically connects to complementary recess 135, complementary conductive connector 222 mechanically connects to hollow snap connector 134 by means of protruding elements 222A, and complementary conductive connector 222 electrically connects to complementary recess 135 by means of conductive snap 222B.

It should be emphasized that complementary conductive connector 222 can be directly attached to complementary recess 135 when no personal panel is used in the orthosis.

Another aspect of the present invention relates to the electrodes of the orthosis. Hydrogel electrodes are commonly used for electrical stimulation applications, as well as for other applications. The conductive hydrogel layer is used to ensure and improve the electrical contact between the electrode and the skin surface.

Often, after a period of time of using the electrode, the hydrogel layer tends to peel off from the electrode edges surface. This is due, apparently, to the pull and shear stress acting on the hydrogel layer, and to the weakening of the hydrogel layer attachment to the underlying surface thereof. This problem is especially prevalent when a self-adhesive hydrogel electrode is used, and when the electrodes are positioned under an overlying layer, such as when positioned inside an orthosis or a sleeve.

According to the present invention, in order to eliminate the disintegration of the edges of the hydrogel layer from the underlying layer, the hydrogel layer is mechanically attached to the underlying electrode surface. Referring now to an exemplary embodiment provided in FIG. 14, the inventive electrode assembly 360 has a disk-shaped electrode 370 having a hydrogel layer 372 and an underlying electrode surface layer 374. Mechanical attachment is achieved by providing an additional, thin layer or film, such as first film ring 376, disposing hydrogel layer 372 between underlying layer 374 and film ring 376, and attaching or bonding first film ring 376 to underlying layer 374. Electrode 370 is adapted such that hydrogel layer 372 is for facing, and adhering to, the skin surface of the user, while underlying layer 374 is for facing the orthosis. The mechanical attachment can be achieved by an ultrasonic process, or by other processes known to those skilled in the art, including, but not limited to, sewing, gluing, etc. In this manner, hydrogel layer 372 is confined between film ring 376 and underlying electrode surface layer 374.

Alternatively or additionally, first film ring 376 can be attached to an additional thin layer or film, such as second film ring 378. The attachment to second film ring 378 may improve the connection between first film ring 376 and electrode 370. The attachment of first film ring 376 to second film ring 378 may be performed by ultrasonic welding. It must be emphasized that is often not possible to make an ultrasonic weld between typical electrode materials and an adjacent surface.

An additional layer 380 having attachment points or an attachment mechanism 382 may also be connected to electrode 370, on the side of underlying electrode surface layer 374, so as to improve the attachment of the electrode to the electrode base or to any underlying layer. In the exemplary embodiment provided in FIG. 14, additional layer 380 is a ring, and attachment mechanism 382 is of the hook-and-loop (e.g., Velcro®) variety. Such an attachment mechanism is instrumental in preventing an electrode from sticking to the skin and becoming detached from the electrode base during removal of the base (or sleeve) from the skin surface. The hook-and-loop material on additional layer 380 may also improve the attachment of second film ring 378 to electrode 370.

In a presently preferred embodiment, first film ring 376 and second film ring 378 each have a thickness of about 50-200 microns. A thickness of about 125-175 microns is presently preferred. The presently preferred material of construction is clear polypropylene.

Another aspect of the present invention is a foot sensor device for gait enhancement, having a fastening unit, for securing the electronic communication unit to the shoe of the user, in a substantially fixed position, during gait of the user.

Figure 15A:
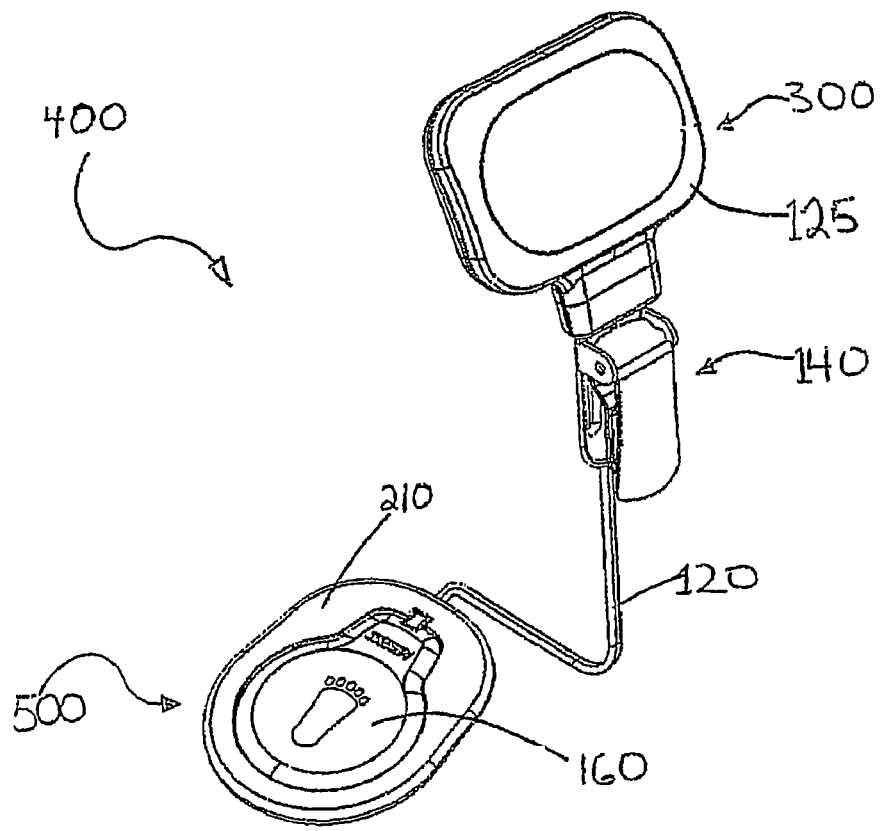
FIG. 15a is a perspective view of the inventive foot sensor device.

FIG. 15a is a perspective view of the inventive foot sensor device 400 for a gait-enhancing orthosis. Foot sensor device 400 includes a sensor unit 500 having a sensor casing 210, in which is disposed a sensor element 160, a communication unit 300 enclosed by housing 125, and wiring (wire or cable) 120 for mechanically and electrically connecting sensor element 160 and communication unit 300. Foot sensor device 400 further includes a fastening unit such as clamp unit 140, rigidly or at least semi-rigidly attached to communication unit 300, for attaching communication unit 300 to the user's shoe, and more typically, to the rim of the user's shoe (see FIG. 15b hereinbelow). It should be stressed that sensor element 160 of inventive foot sensor device 400, in contrast to RF-based foot sensor devices of the prior art, is substantially mechanically independent of communication unit 300. The advantages of this attribute are elaborated hereinbelow.

As used herein in the specification and in the claims section that follows, the term "substantially mechanically independent" refers to two components, electrically and mechanically connected, and physically set apart from one another, the components having substantially no constraint when moved towards one another. A typical example of such substantially mechanically independent components is communication unit 300 and sensor casing 210, connected by a flexible conductive wire.

Figure 15B:
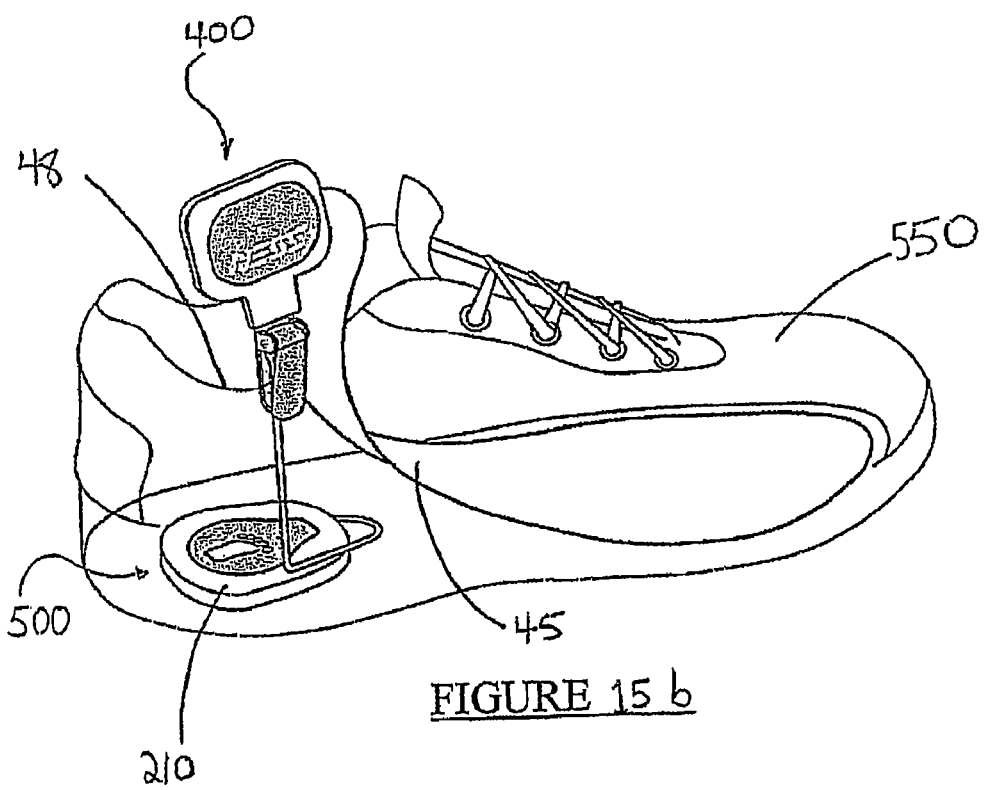
FIG. 15b is a schematic, three-dimensional view of the inventive foot sensor device, the sensor unit being disposed underneath the shoe insole, and the communication unit being mounted on the shoe rim.

Generally in the prior art, the foot pressure switch, or the sensor, is either permanently disposed in the shoe, or disposed in a small pouch of a sock, as in the above-described Acti-Gait® system. As shown in FIG. 15b, by sharp contrast, sensor unit 500 is preferably placed under an inner sole 45 of a shoe 550, beneath the heel area. Sensor casing 210 can be removed or repositioned with facility, by lifting up or removing inner sole 45.

Figure 15C:
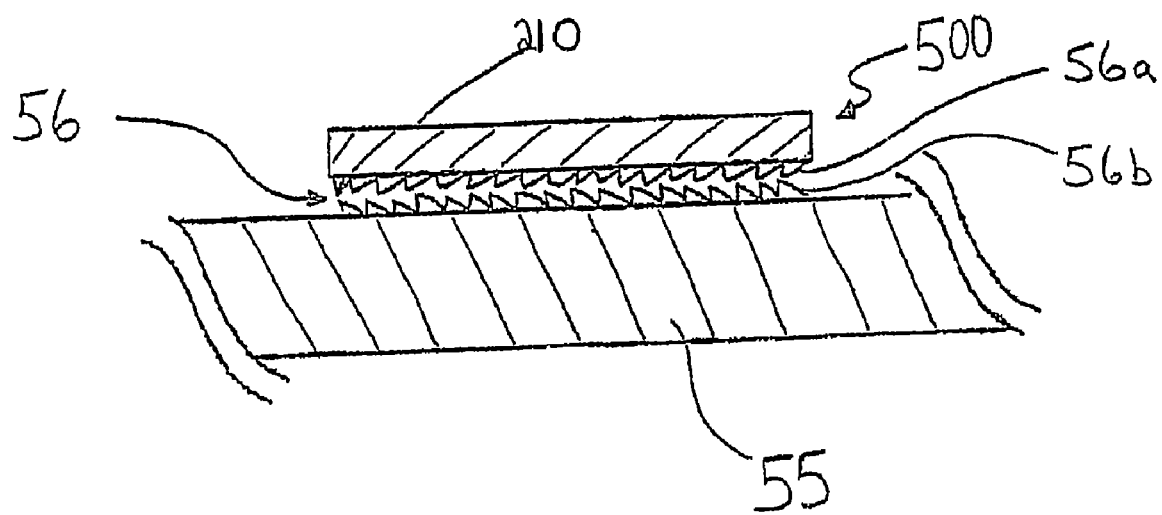
FIG. 15c is a partial cross-sectional view of a shoe floor, a sensor casing, and a hook and loop system for affixing the casing to the floor.

As shown in a cross-sectional view in FIG. 15c, sensor unit 500 may advantageously secured to the floor 55 of the shoe by a hook and loop system 56 such as Velcro®. By way of example, hooks 56a of hook and loop system 56 may be attached to sensor casing 210, and loops 56b may be attached to floor 55. In particular cases, sensor casing 210 may also be positioned under the forefoot area of the shoe.

Casing 210 is configured to protect the inner sensor element against mechanical stress and wetness, and is made of two flexible layers, selected such that the upper layer is more flexible than the lower layer. An additional piece of sponge-like material lies between the internal layer and the sensor, providing additional protection to the sensor. The two layers of sensor casing 210 are attached by various means such as ultrasonic welding, RF welding, gluing, heat welding, or pins. Casing 210 is connected to communication unit 300 by means of wiring 120, which is long enough to enable attachment of communication unit 300 to a rim 48 of shoe 550, irrespective of the height of the shoe rim. It should be noted that when the shoe is not worn, foot sensor device 400 can be left attached to shoe 550, such that the user is not challenged with an additional, cumbersome, and unintuitive doffing action, and in subsequent use, a similarly challenging donning action.

The positioning of communication unit 300 above the rim of shoe 550 protects communication unit 300 from being banged and rubbed by external objects, and from exposure to dirt and moisture. Such positioning may also serve to keep communication unit 300 hidden under the trousers, which is aesthetically desirable and, perhaps more importantly, protects communication unit 300 from being caught or bumped during gait.

Moreover, in foot sensor device 400 of the present invention, the height of communication unit 300 on the leg of the user is substantially fixed with the height of the shoe rim. In the above-referenced design patent to Haugland, et al., by sharp contrast, the distance between the communication unit and the sensor unit is determined by the semi-rigid spine connecting therebetween, such that the height of the communication unit is not adjustable. Consequently, the entire communication unit may not extend over the shoe rim in boots and other high-rimmed shoes, and the communication unit may be disposed at a disadvantageously distance from the shoe rim in low shoes.

Another advantage of the foot sensor device 400 of the present invention is that wiring 120 is thin and is easily contained within the shoe. The wide spine of the device disclosed by Haugland, et al., is bulky, such that the user is subject to the distraction of sensing the spine within the shoe, even to the point of experiencing discomfort.

Perhaps most significantly, foot sensor device 400 may be advantageously fixed to the rim of the shoe in a semi-permanent fashion, i.e., even during those periods in which the user is not undergoing neuroprosthetic gait enhancement. Thus, prior to activating or reactivating the device, no additional donning procedure is required.

Figure 16:
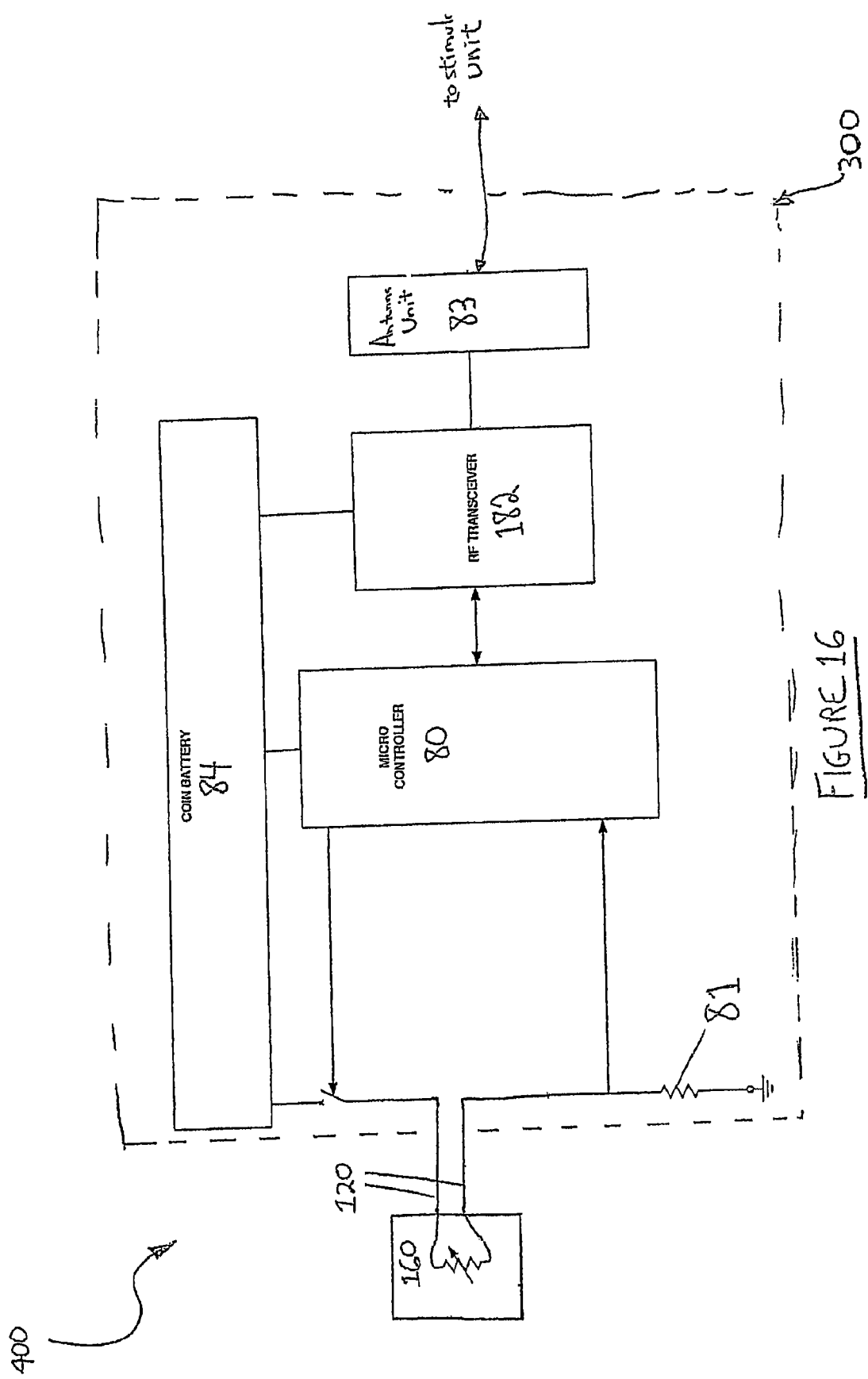
FIG. 16 is a schematic electronic diagram of the inventive foot sensor device.

FIG. 16 is a schematic electronic diagram of inventive foot sensor device 400. Sensor element 160 is connected to, and preferably powered by, electronics or communication unit 300 by means of wiring 120. Communication unit 300 includes a microcontroller 80, a radio frequency (RF) transceiver 82, and an antenna unit 83 having a matching network for converting the signal from the wired medium to a wireless medium, and from the wireless medium to the wired medium.

The resistance of sensor element 160 changes with the force applied thereon. In order to measure the actual resistance of sensor element 160, foot sensor device 400 is equipped with a voltage divider consisting of sensor element 160 and a bias resistor 81 preferably disposed in unit 300. When a voltage is applied to the voltage divider, the voltage is divided according to the resistance ratio between sensor element 160 and bias resistor 81. This voltage is measured in order to assess the resistance of sensor element 160.

Communication unit 300 is also equipped with a small coin battery 84 that provides power to microcontroller 80, RF transceiver 82, and sensor element 160.

Microcontroller 80 controls and monitor the operation of foot sensor device 400 and executes the algorithms thereof. Preferably, microcontroller 80 communicates with RF transceiver 82 via a Serial Peripheral Interface (SPI).

Figure 17:
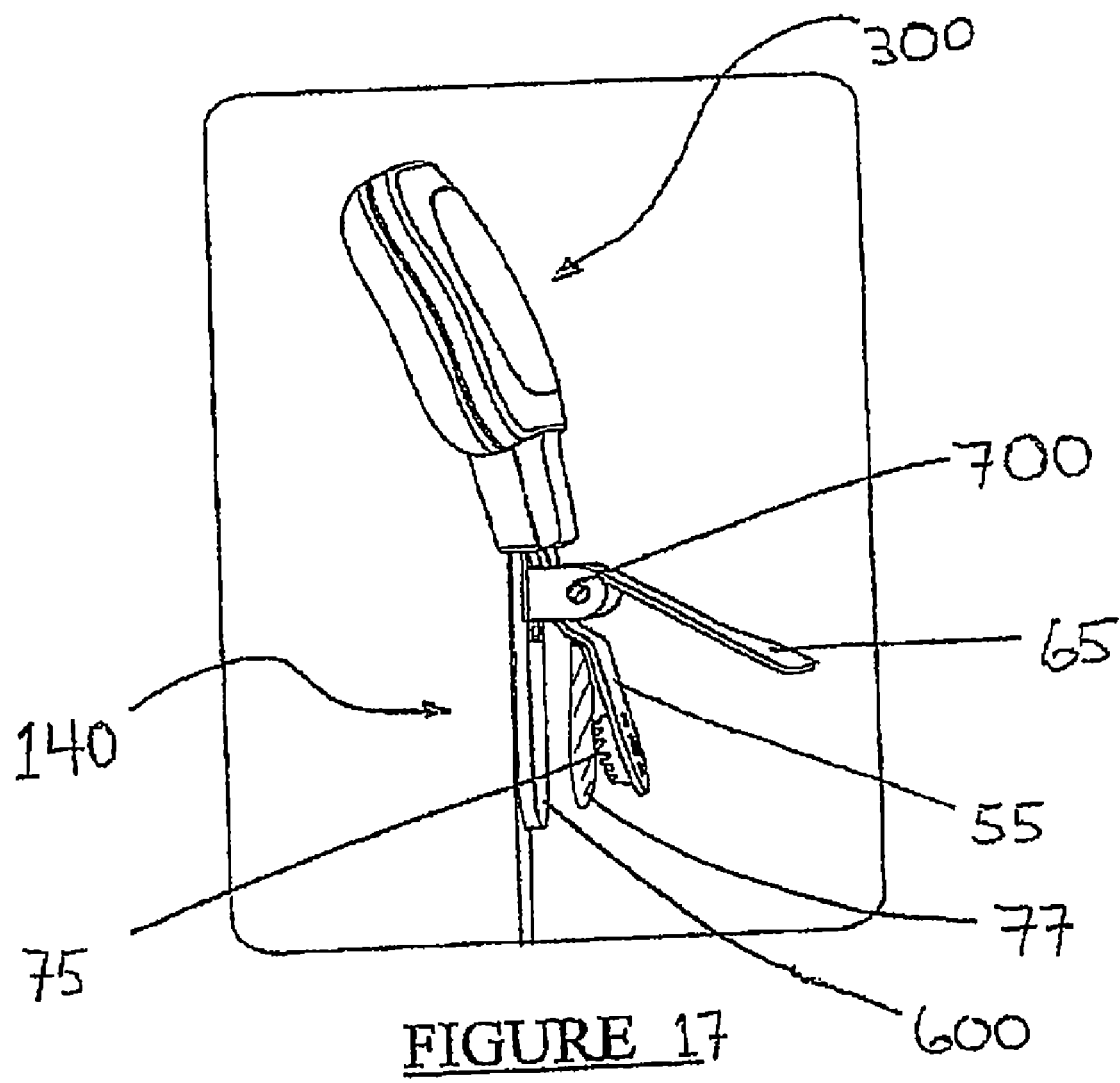
FIG. 17 is a perspective side view of the communication unit and the clamp associated therewith, the clamp disposed in an open position.
Figure 18:
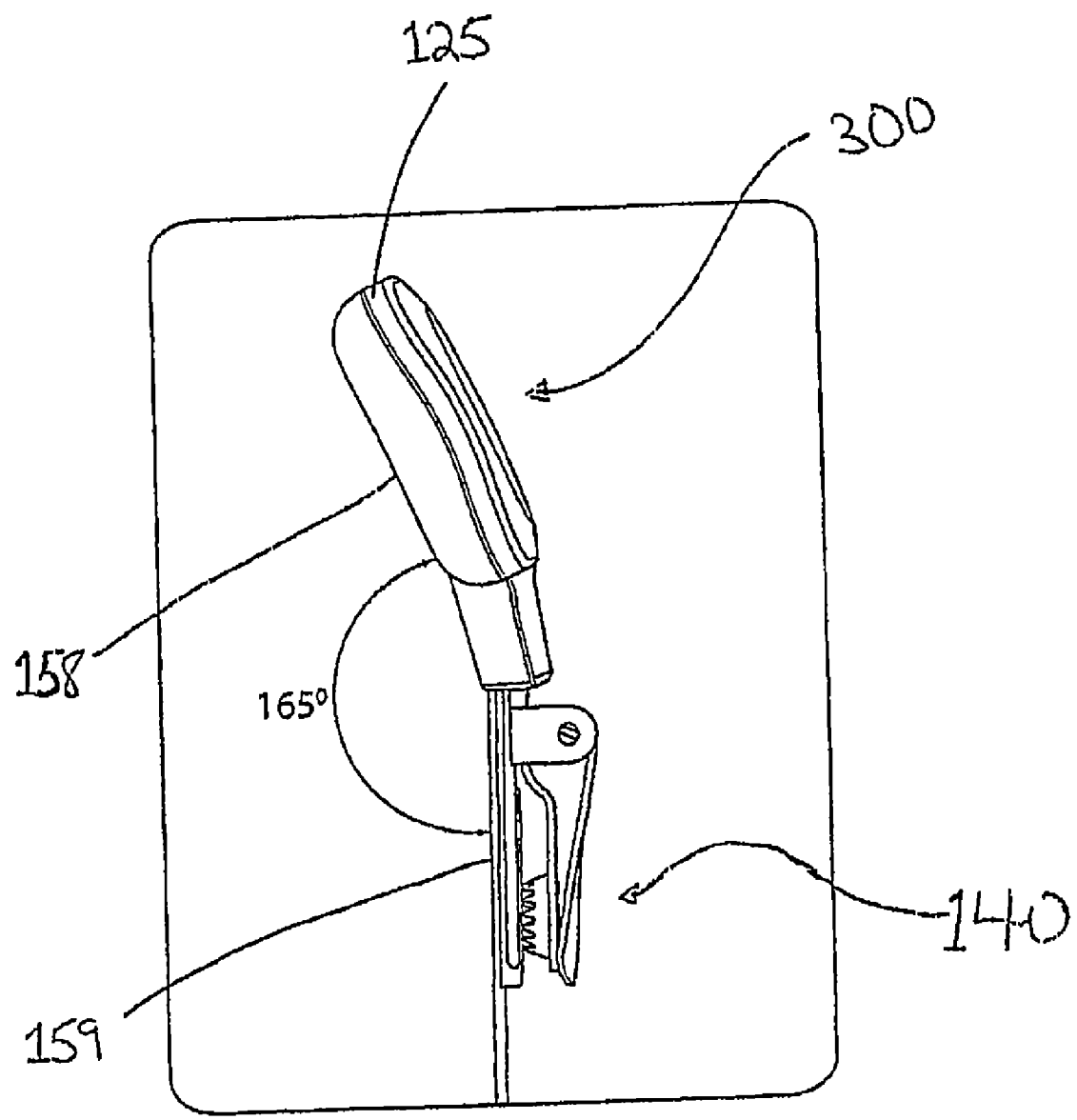
FIG. 18 is another perspective side view of the communication unit and the clamp associated therewith, the clamp disposed in a closed position.

Referring now to FIGS. 17 and 18, clamp unit 140 is designed for facile and fully reversible attachment and disattachment of communication unit 300 to the rim of a shoe, such that even a hemiplegic patient can perform these functions using a single hand.

Clamp unit 140 includes an external (i.e., distal to the shoe) arm or jaw 55, an internal arm or jaw 600 and a locking lever 65 having a fulcrum 700 for closing and locking together jaws 55 and 600. Preferably, when clamp unit 140 is in an open position, jaws 55 and 600 are positioned in a pre-defined angle. The magnitude of this angle is important, since it determines the opening range of the clamp, to fit shoe rims of varying width.

Preferably, arm 55 includes a spring adapted such that clamp unit 140 is in a normally open condition.

Preferably, clamp unit 140 is further adapted such that when clamp unit 140 is in the closed position, with no article clamped between jaws 55 and 600, a small gap (typically less than or equal to one millimeter) exists between jaws 55 and 600. This eliminates the need to apply a strong force in opening clamp unit 140.

Teeth 75, disposed on at least one of jaws 55 and 600, ensure a firm grip of clamp unit 140 on the shoe rim, such that clamp unit 140 is inherently adaptable to a wide range of rim thicknesses, contours, and textures. Locking lever 65 serves to fix jaws 55 and 600 to the rim of the shoe.

Internal jaw 600 has a thin profile, such that when disposed inside shoe 550 of the user, internal jaw 600 does not to protrude into the skin of the foot and cause discomfort to the user.

Preferably, a reversibly attached, thin, flexible spacer such as spacer 77 is disposed between jaws 55 and 600, in order to protect the rim of the shoe from the local pressures exerted by teeth 75.

Typically, clamp unit 140 is permanently and rigidly associated with communication unit 300. The connection of clamp unit 140 to communication unit 300 is achieved by an element (not shown) that, from clamp unit 140, extends into communication unit 300 and is secured therein.

It must be emphasized that other embodiments of clamps and fastening units will be apparent to those skilled in the art. For example, the clamp could have fixed arms that grip the shoe rim by a constant spring force, without an opening and closing mechanism.

As used herein in the specification and in the claims section that follows, the term "casing", with respect to the electronic communication unit, refers to the at least semi-rigid casing enveloping at least a portion of the electronic communication unit.

As used herein in the specification and in the claims section that follows, the term "housing" and the like, with respect to the electronic communication unit, is meant to include any rigid or semi-rigid projections of the housing, and is meant to include any elements that are at least semi-rigidly attached to the casing. The term "housing" is specifically meant to include rigid and semi-rigid spines attached to the electronic communication unit, such as the element disclosed in U.S. Pat. No. D 494,273 to Haugland, et al.

As used herein in the specification and in the claims section that follows, the term "shoe" is meant to include boots, slippers, or sandals having an at least semi-rigid position for fastening the fastening unit. Typically, this at least semi-rigid position is the rim of the shoe. Preferably, the shoe has rigid or at least semi-rigid sole and a covering for firmly containing a foot therein.

Figure 19:
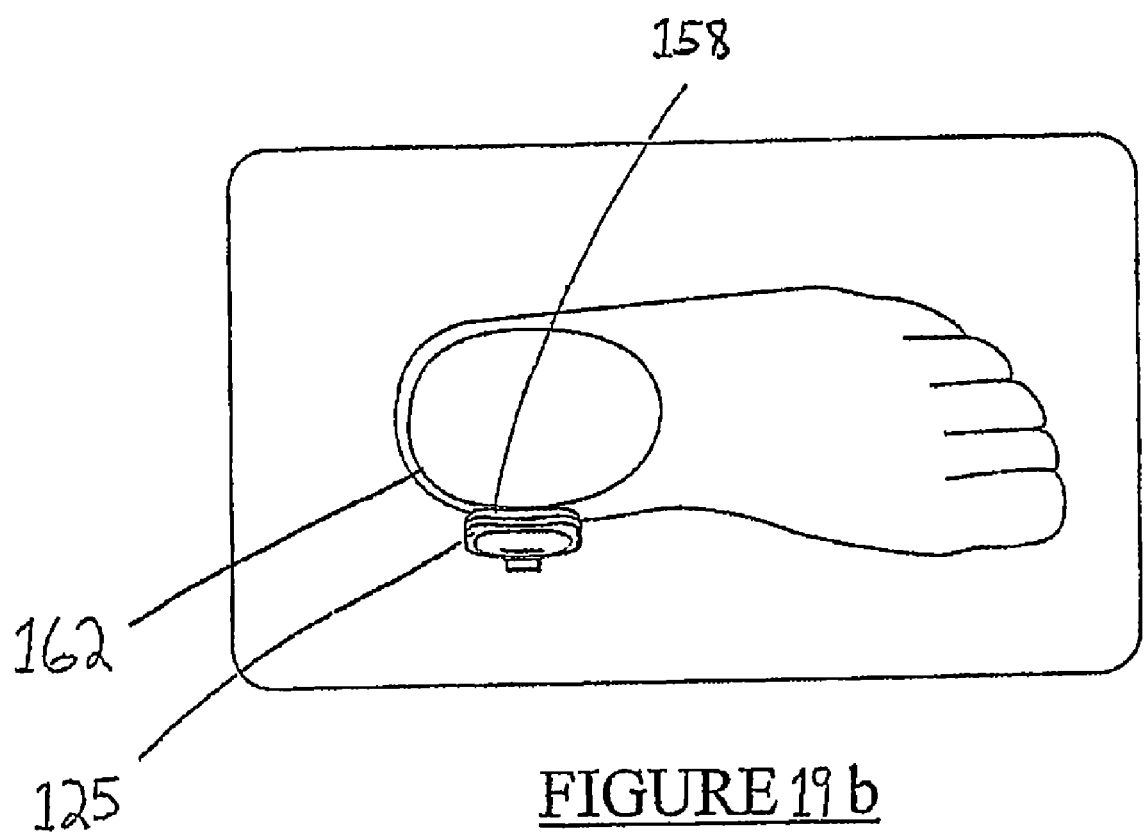

FIG. 19a is a schematic, three-dimensional view of the inventive foot sensor device 400 mounted on shoe 550. FIG. 19b is a schematic, three-dimensional top view of FIG. 19a. These figures collectively show an inner face 158 of housing 125 (of communication unit 300) hugging an inner calf 162 of the user. The surface of the casing has a small, predetermined curvature that is designed to match and hug the natural curvature of the leg, thereby improving comfort and preventing chafing of communication unit 300 against the skin.

Flexibility, or a degree of freedom, with respect to the leg, is imparted to communication unit 300 by the flexibility of the shoe rim.

Alternatively, communication unit 300 may be connected to clamp 140 by means of an elastomeric hinge to allow extra flexibility of the casing of communication unit 300 against the foot. The electronic casing may also include a hinge that allows calibrating the angle of the electronic casing against the foot for personal adjustment with respect to specific users and specific shoe dimensions.

Referring back to FIG. 18, inner face 158 of housing 125 and an inner face 159 of clamp unit 140 (internal arm 600) form an angle of about 165°. After extensive tests were performed on users having widely varying physical characteristics, the inventors discovered that within a narrow range of angles, chafing and pressure of housing 125 against the leg of the user is substantially insignificant. In addition, within this narrow range of angles, housing 125 does not protrude away from the leg in an unreasonable fashion, such that housing 125 is protected from bumping into, or being caught by objects during gait. We have found this narrow range of angles to be between 150° and 175°. More preferably the range of angles is between 155° to 160° and 175°, and most preferably, the range is between 160° and 170°.

Figure 20:
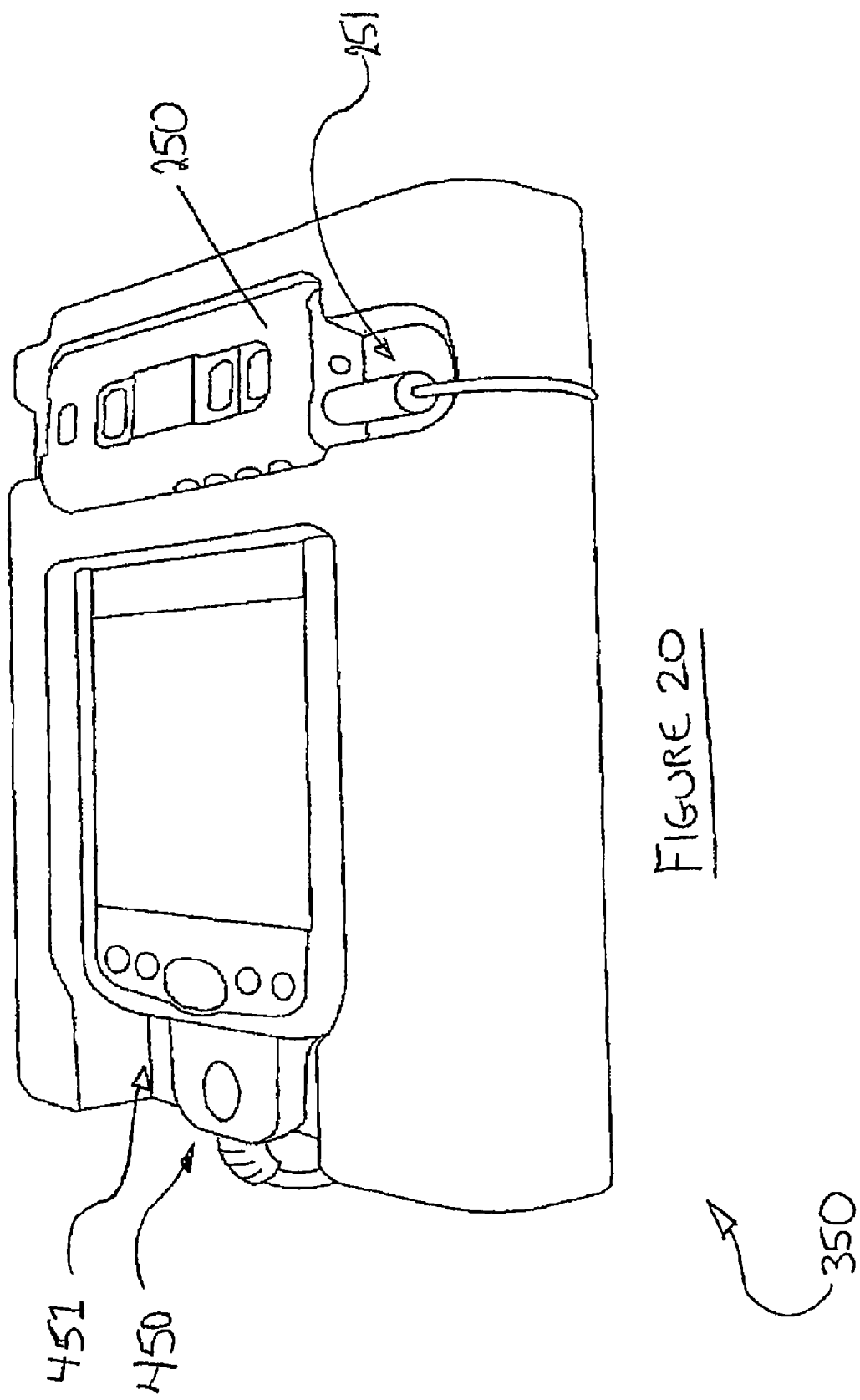
FIG. 20 is a schematic perspective drawing of an inventive configuration cradle for on-line configuration of the system by the clinician.

It is often desirable to configure the inventive FES orthosis system on-line, i.e., during usage of the orthosis by the patient. FIG. 20 is a schematic perspective drawing of an inventive configuration cradle 350 for on-line configuration of the system by the clinician. Configuration cradle 350 has a mechanical and electrical receptacle 251 for receiving control unit 250, and a mechanical and electrical receptacle 451 for receiving a personal digital assistant (PDA) 450. Control unit 250 is described in greater detail hereinabove, with respect to FIG. 11.

As is known in the art, PDAs such as PDA 450 are small, hand-held portable computers having a Central Processing Unit (CPU) and electronic memory, and are generally used for storing and organizing information and for providing tools for everyday tasks. The PDA currently being used in conjunction with this aspect of the present invention is operated by the "Windows Mobile 5" software of Microsoft®. PDA 450 preferably has a database containing a gait log and various personal parameters of the patient, and is programmed to configure the stimulation parameters of the electrical stimulation system.

Configuration cradle 350 enables PDA 450 and control unit 250 to be in digital (and preferably electrical) communication, such that the orthosis system can be configured on-line by the clinician during actual usage of the orthosis by the patient. In this arrangement, control unit 250 actually serves as the transmitter of PDA 450, enabling PDA 450, via control unit 250, to communicate with and command the other components of the electrical stimulation system.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method, comprising:
    disposing a connector of a stimulation electrode assembly through an opening defined by a detachable layer;
    reversibly coupling the connector of the stimulation electrode assembly to a connector disposed on an inner face of a frame;
    coupling the detachable layer to the inner face of the frame, the detachable layer constructed from a soft material; and
    disposing the frame about a limb segment of a body such that the detachable layer is in contact with a portion of the limb segment, and an electrical stimulation electrode of the stimulation electrode assembly is in contact with at least one stimulation point on a surface of the body associated with a muscle.

2. The method of claim 1, wherein the coupling includes removably coupling a fastener of the detachable layer to a fastener of the frame.

3. The method of claim 1, wherein the coupling includes removably coupling a hook and loop fastener of the detachable layer to a corresponding hook and loop fastener of the frame.

4. The method of claim 1, further comprising:
    adjusting a position of the electrical stimulation electrode relative to an inner surface of the detachable layer after the coupling.

5. The method of claim 1, further comprising:
    removing the detachable layer from the inner face of the frame after the disposing.

6. A method, comprising:
    positioning a surface electrode against an electrode base on an inner layer, the inner layer coupled to a frame, the frame including a retention portion and a mounting portion, the retention portion configured to retain the frame about the portion of a limb, the mounting portion coupled to an electrical stimulator;
    electrically coupling the surface electrode to the electrical stimulator via a connector assembly, at least a portion of the connector assembly disposed within a connector opening defined by the frame; and
    disposing the frame and the inner layer about the portion of a limb such that the electrode base is disposed at a predetermined position relative to the portion of the limb, the predetermined position being adjacent a muscle such that electrical stimulation applied at the predetermined position via the surface electrode results in dorsiflexion of a foot.

7. The method of claim 6, wherein the inner layer is reversible.

8. The method of claim 6, wherein the connector assembly includes a first connection member coupled to an intermediate layer and a second connection member coupled to the inner layer.

9. The method of claim 6, wherein:
    the retention portion includes a first member and a second member, an end portion of the first member spaced apart from an end portion of the second member; and
    the disposing includes disposing the frame and the inner layer about the portion of the limb such that the first member and the second member exert a force about the portion of the limb.

10. The method of claim 6, wherein:
    the retention portion includes a first member and a second member, an end portion of the first member spaced apart from an end portion of the second member to define an opening; and
    the disposing includes disposing the frame and the inner layer about the portion of the limb by placing a the portion of the limb through the opening.

11. The method of claim 6, wherein the retention portion includes a first member and a second member, an end portion of the first member spaced apart from an end portion of the second member to define an opening, the disposing includes disposing the frame and the inner layer about the portion of the limb by placing the portion of the limb through the opening, the method further comprising
    coupling a fastening strap across the opening.

12. The method of claim 11, wherein the coupling the fastening strap includes disposing a loop member of the fastening strap about a protrusion on the frame.

13. A method, comprising:
    placing a portion of a limb through a frame opening defined by a first member of a frame assembly and a second member of the frame assembly, an end portion of the first member spaced apart from an end portion of the second member to define the frame opening, the frame assembly including a surface electrode coupled to an inner surface of the frame assembly such that the surface electrode is disposed at a predetermined position relative to the portion of the limb when the frame assembly is disposed about the portion of the limb, the predetermined position being adjacent a muscle such that electrical stimulation applied at the predetermined position via the surface electrode results in dorsiflexion of a foot; and
    coupling a fastening strap across the opening.

14. The method of claim 13, wherein the coupling the fastening strap includes disposing a loop member of the fastening strap about a protrusion on the frame assembly.

15. The method of claim 13, wherein the coupling the fastening strap includes disposing at least a portion of the fastening strap about a stimulator coupled to the frame assembly.

16. The method of claim 13, wherein the frame assembly includes an electronic stimulator configured to produce a current to the surface electrode, the method further comprising:

electrically coupling the surface electrode to the stimulator via a connector assembly, at least a portion of the connector assembly disposed within a connector opening defined by the frame assembly.

17. The method of claim 13, wherein the the frame assembly includes a frame member and an inner layer reversibly coupled to the frame member, the surface electrode coupled to the inner layer, the frame member including the first member and the second member.

* * * * *